United States Patent [19]

Holland et al.

[11] Patent Number: 4,808,734

[45] Date of Patent: Feb. 28, 1989

[54] 16-CYCLOALKYL-7-FLUORO-PROSTACYCLINS

[75] Inventors: George W. Holland; Perry Rosen, both of North Caldwell, N.J.; Hans Maag, Menlo Park, Calif.; Ferdinand Lee, Teaneck, N.J.

[73] Assignee: Hoffmann-La Roche Inc., Nutley, N.J.

[21] Appl. No.: 936,569

[22] Filed: Dec. 1, 1986

[51] Int. Cl.$^4$ .................................. C07D 307/935
[52] U.S. Cl. ........................ 549/465; 549/311; 560/121
[58] Field of Search .......................... 549/465

[56] References Cited

U.S. PATENT DOCUMENTS

| | | | |
|---|---|---|---|
| 4,472,428 | 9/1984 | Toru et al. | 549/465 |
| 4,558,142 | 12/1985 | Holland et al. | 549/465 |
| 4,634,782 | 1/1987 | Holland et al. | |
| 4,699,989 | 10/1987 | Arata et al. | |

FOREIGN PATENT DOCUMENTS

| | | |
|---|---|---|
| 0054795 | 6/1982 | European Pat. Off. . |
| 0229844 | 7/1987 | European Pat. Off. . |
| 3208880 | 9/1982 | Fed. Rep. of Germany . |
| 60-243079 | 12/1985 | Japan ................... 549/465 |
| 1513913 | 6/1978 | United Kingdom . |
| 07538 | 12/1986 | World Int. Prop. O. . |

OTHER PUBLICATIONS

Bindra et al., Prostaglandin Synthesis, Academic Press Inc., New York, p. 461, 469–470, (1977).

*Primary Examiner*—Mary C. Lee
*Assistant Examiner*—Bernard I. Dentz
*Attorney, Agent, or Firm*—Jon S. Saxe; George M. Gould; William H. Epstein

[57] ABSTRACT

16-Cycloalkyl-7-fluoro prostacyclins having a 16 lower alkyl or fluoro substituent useful as blood platelet anti-aggregating agent, vasodilators, cyto protective lowering agents, anti-ulcerogenic agent and for treating peripheral vascular diseases such as schleroderma.

13 Claims, No Drawings

16-CYCLOALKYL-7-FLUORO-PROSTACYCLINS

SUMMARY OF THE INVENTION

In accordance with this invention, compounds of the formula

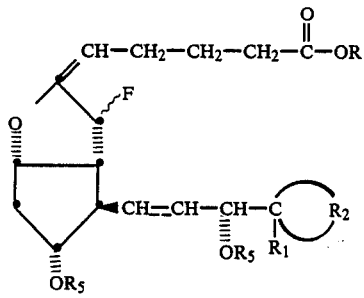

wherein R is hydrogen or lower alkyl; $R_5$ is hydrogen or lower alkanoyl; $R_1$ is lower alkyl or fluoro and $R_2$ taken together with its attached carbon atoms form a cycloalkyl ring of from 3 to 7 carbon atoms and the dotted bond can be optionally hydrogenated and compounds of the formula

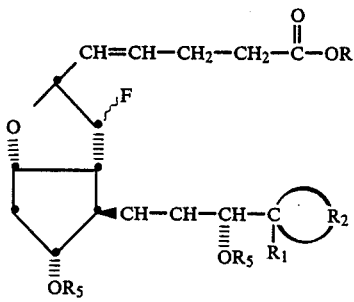

wherein R, $R_1$, $R_2$ and $R_5$ are as above and the dotted bond can be optionally hydrogenated and salts thereof as well as optical antipodes, racemates, and diasteroisomers thereof are useful as blood platelet anti-aggregating agents, vasodilators, cytoprotective agents and anti-ulcerogenic agents. In particular, the compound of formula I are particularly useful when administered topically to treat peripheral vascular diseases such as schleroderma.

The compounds of formula I and II above can be prepared by first reacting a compound of the formula

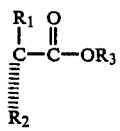

where $R_1$ and $R_2$ are as above and $R_3$ is lower alkyl, with a compound of the formula:

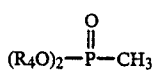

wherein $R_4$ is lower alkyl to produce a compound of the formula:

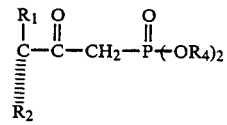

wherein $R_1$, $R_2$ and $R_4$ are as above.

The compound of formula V is convented, in accordance with this invention, to the compounds of formula I and II.

DETAILED DESCRIPTION OF THE INVENTION

As used throughout this application, the term "lower alkyl" includes both straight chain and branched chain alkyl groups having from 1 to 7 carbon atoms such as methyl and ethyl. As also used herein, the term "lower alkanoic acids" comprehends an alkanoic acid of from 1 to 7 carbon atoms such as formic acid and acetic acid. The term "lower alkanoyl" designates the monovalent radical formed from a lower alkanoic acid by removal of the OH group on the COOH moiety. Among the preferred alkanoyl groups are acetyl, pivaloyl, butyryl, propionyl with acetyl being preferred. As further used herein, the the term "halogen" or "halo", unless otherwise stated, comprehends fluorine, chlorine, bromine and iodine. Alkali metal includes all akali metals such as lithium, sodium and potassium.

The term "cycloalkyl" designates saturated ring moieties containing only carbon and hydrogen ring atoms having from 3 to 7 carbon atoms in the ring such as cyclopropyl, cyclopentyl, cyclohexyl, cycloheptyl with rings of from 5 to 6 carbon atoms being preferred.

In the process of this invention, all compounds having one or more asymmetric carbon atoms can be produced as racemic mixtures. These racemic mixtures which are obtained can be resolved at the appropriate steps in the process of this invention by methods well known in the art whereupon subsequent products may be obtained as the corresponding optically pure enantiomers. On the other hand, the claimed optically active anantiomer, racemates or diasteroisomers of formula I can be produced depending upon the form of the compound of formula III utilized as a starting material.

In the pictorial representation of the compounds given throughout this application, a thickened taper line (——■) indicates a substituent which is in the beta-orientation (above the plane of the molecule), a dashed line (/////) indicates a substituent which is in the alpha-orientation (below the plane of the molecule) and a wavy line (∼∼∼) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, which can be unsubstituted or substituted in one or more positions with a lower alkylenedioxy, nitro, halo, a lower alkyl or a lower alkoxy substituent, and polynuclear aryl groups such as naphthyl, anthryl, phenanthryl, etc., which can be unsubstituted or substituted with one or more of the aforementioned groups. The preferred aryl groups are the substituted and unsubstituted mononuclear aryl groups, particularly phenyl.

The term "ether protecting group removable by acid catalyzed cleavage" designates any ether group for protecting a hydroxy group which, upon acid catalyzed cleavage yields the free hydroxy group. A suitable ether protecting group is, for example, the tetrahydropyranyl ether, or 4-methoxy-tetrahydropyranyl ether. Others are arylmethyl ethers such as benzyl, benzylhydryl, or trityl ethers or alpha-lower alkoxy lower alkyl ether, for example, methoxymethyl or tri(lower alkyl)silyl ethers such as trimethyl silyl ether; diphenyl-t-butyl silyl ether or dimethyl-tert-butyl silyl ethers. The preferred ether protecting the groups which are removed by acid catalyzed cleavage are t-butyl and tetrahydropyranyl ethers as well as the tri(lower alkyl and/or aryl)silyl ethers, particularly dimethyl-tert-butyl silyl ether and diphenyl-t-butyl silyl ether. Acid catalyzed cleavage is carried out by treatment with an organic or inorganic acid. Among the preferred inorganic acids are the mineral acids such as sulfuric acid, hydrohalic acid, etc. Among the preferred organic acids are lower alkanoic acids such as acetic acid, para-toluene sulfonic acid, etc. The acid catalyzed cleavage can be carried out in an aqueous medium or in an organic solvent medium. Where an organic acid or alcohol is utilized, the organic acid or alcohol can be the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The term "ester protecting group" denotes ester protecting groups where the hydroxy substituent is protected by esterification with an organic acid to form a ester which upon hydrolysis yields the free hydroxy substituent. Among the preferred hydrolizable esters which can be utilized to protect the hydroxy group are those esters formed by reacting the hydroxy group with a lower alkanoic acid containing from 1 to 7 carbon atoms present as acetic acid, propionic acid, butyric acid, as well as aroic acids such as benzoic acid and aryl lower alkanoic acids where aryl is defined as above and the lower alkanoic acid contains from 2 to 7 carbon atoms.

The compounds of formula I and II above including their salts, optical antipodes, racemates and diasteroisomers can have activity as blood platelet anti-aggregating agents, anti-ulcerogenic, vasodilator agents and cytoprotective agents and are active to treat claudication. The compounds of formula I and II above including their salts, optical antipodes and racemates due to their inherent stability can be administered orally, topically or intravenously.

When administered orally, the compounds of formulae I and II or their pharmaceutically acceptable salts as well as racemates and diasteroisomers thereof can be used in a variety of pharmaceutical preparations. In these preparations, these compounds or their salts are administerable in the form of tablets, pills, powders, capsules, and in other suitable forms. The pharmaceutical preparations which contain the compounds of formulae I-A and I-B or their pharmaceutically acceptable salts are conveniently formed by admixing them with a non-toxic pharmaceutical organic or inorganic carrier. Typical of pharmaceutically acceptable carriers are, for example, water, gelatin, lactose, starch, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will, of course, vary with the particular novel compound employed because of the very potency of the compounds, the chosen route of administration and the size of the recipient. The dosage administered is not subject to definite bounds but it will usually be in effective amounts of the pharmacologically function of the prostacyclin. Representative of a typical method for administering the prostacyclin compounds of formulae I or phamaceutically acceptable salts thereof is by oral administration in the form of tablets or capsules. By this route, the prostacyclins of formulae I and II or their salts can be administered at a dosage of 0.1 micrograms to 0.50 milligrams per day per kilogram of body weight.

The compounds of formula I and II, and their salts as well as their optical antipodes, racemates, and diasteroisomers can be administered topically. Topical administration is especially well suited for preventing or treating claudication to enhance red blood cell deformability. In this manner these compounds enhance red blood cell circulation by promoting red blood cell deformability so that these cells can pass through nutrient vessels having small diameters. This activity makes these compounds useful in treating peripheral vascular diseases such as schleroderma. Also these compounds can be topically applied to lower blood pressure.

For topical administration to the skin the aforementioned compounds their optical antipodes, racemates or their salts are preferably prepared as ointments, tinctures, patches, creams, gels, solutions, lotions, sprays, suspensions, and the like. In fact, any conventional composition utilized for application to the scalp or skin can be utilized in accordance with this invention. Among the preferred methods of applying the composition containing the agents of this invention is in the form of gels, lotions, cream solutions and patches. The pharmaceutical preparation for topical administration to the skin can be prepared by mixing the aforementioned active ingredient with non-toxic, therapeutically inert, solid or liquid carriers customarily used in such preparations. These preparations should contain at least about 0.0005 percent by weight, of the active ingredients based upon the total weight of the composition. However, the active ingredient, the compound of formula I may be used in topical compositions in amounts significantly exceeding 10 percent i.e. up to 20% by weight. It is generally preferred that these preparations contain from about 0.01 to 10 percent by weight of the active ingredient based upon the total weight of the topical composition. While it is preferred to apply these preparations once or twice daily to the skin, these preparations can be applied according to the need of the patient. In carrying out this invention, the active ingredient can be applied in an aqueous solution or an alcohol solution such as ethyl alcohol.

In preparing the topical preparations described above additives such as preservatives, thickeners, perfumes, and the like conventional in the art of pharmaceutical compounding of topical preparations can be used. In addition, conventional antioxidants or mixtures of conventional antioxidants can be incorporated into the topical preparations containing the aforementioned active agent. Among the conventional antioxidants which can be utilized in these preparations are included N-methyl-alphatocopherolamine, tocopherols, butylated hydroxyanisole, butylatedhydroxytoluene, ethoxyquin and the like. Cream-base topical formulations containing the active agent, used in accordance with this invention, are composed of aqueous emulsions containing a fatty acid alcohol, a semi-solid petroleum hydrocarbon, 1,2-ethyleneglycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of fatty acid alcohol, a semisolid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are derived from the reduction of a long-chain saturated fatty acid of at least 4 carbon atoms. Also, conventional perfumes and lotions generally utilized in topical preparation for the hair can be utilized in accordance with this invention. Furthermore, if desired, conventional emulsifying agents can be utilized in the topical preparations of this invention.

The effectiveness of the compounds of this invention as anti-claudication agents which enhance red blood cell circulation through promoting deformability can be seen by the results of testing the following compound of this invention.

Compound A—[3S-[(Z),3alpha,3a alpha,4alpha(-1E,3R*),5-beta 6a alpha]]-5-[3-fluorohexahydro-5-hydroxy-4-[3-hydroxy-3-(1-methyl-cyclohexyl)-1-propenyl]-2H-cyclopenta[b]furan-2-ylidene]pentanoic acid, sodium salt as compared to $PGI_2$, methyl ester in enhancing red blood cell deformability. In this test, red blood cellular deformability is assessed by forcing a red blood cell suspension through a microporous membrane and measuring the back pressure developed as cells stack up against it. If a suitable pore size is chosen, the resulting back pressure will be larger when the red blood cells are less deformable relative to the resulting back pressure for red blood cells having natural deformability. In the test, a group of normal subjects and patients with schleroderma, were bled by clean venepuncture, and blood was collected into dipotassium ethylenediamine tetraacetic acid. Specimens were centrifuged at 600 g for 10 min to sediment the red cells; both supernatant and buffy coat were pipetted off, and the red cells resuspended in millipore filtered particle free phosphate buffer (0.14M pH 7.4). The cells were washed similarly 2 more times to deplete plasma proteins, white cells and platelets. A full blood count was then performed on the sample. Deformability measurements were performed within 4 hours of sample collection. Fresh phosphate buffer was pumped through an instrument fitted with a nucleopore membrane (3.0 $\mu$) mounted in the membrane holder taking care to eliminate trapped air bubbles. Filtration of the buffer solution on its own was then performed to give the background buffer pressure for the membrane. The red cells were then diluted in buffer to a haematocrit of 0.5% (Hct 0.005) and placed in the glass syringe mounted on the instrument; care was taken to avoid the introduction of air. Filtration of the red blood cell suspension was then initiated to measure the back pressure was then performed. The ratio of red cell pressure to background pressure was defined to be the deformability index (I). Samples were processed in duplicate and if the deformability index differed by more than 0.5, a third determination was carried out and the two values lying within 0.5 of one another were averaged. The patterns of pressure increase were also compared. This enabled the detection of anomalies caused by incorrect mounting of or damaged membranes, and introduction of air bubbles. The influence of Compound A and $PGI_2$ methyl ester was investigated by adding a suitable concentration of these test materials to the red cell diluting buffer.

Some patients with scheroderma appear to show a higher deformability index than the normals studied, indicating more rigid cells. The compounds tested had little or no effect on normal subjects or patients with a normal deformability index (I=2.0–3.0). Patients having a deformability index (I) above the normal range showed an improvement in deformability with Compound A. The results of this test with Compound A and $PGI_2$ methylester are shown in the following table with the results being expressed as the deformability index (I).

TABLE

|  | Control | Concentration | |
|---|---|---|---|
|  |  | $10^{-5}$ M | $10^{-6}$ M |
| Compound A | | | |
| Mean (I) | 2.54 | 2.15 | 2.19 |
| No. of Patients | 4 | 4 | 4 |
| Range (I) | 2.05–2.90 | 1.90–2.50 | 1.75–2.90 |
| $PGI_2$ methyl ester | | | |
| Mean (I) | 2.13 | 2.18 | 2.14 |
| No. of Patients | 2 | 2 | 2 |
| Range (I) | 1.95–2.30 | 1.80–2.55 | 2.15–2.80 |

In preparing the compound of this invention first the compound of formula V is formed by condensing the salt form of the compound of formula IV with the compound of formula III at a temperature of from −80° C. to 25° C. In carrying out this reaction, the compound of formula IV is first converted to its salt form by reaction with a strong base. Any strong base which will form a salt with the compound of formula IV by elimination of proton can be utilized to form this salt. The preferred bases are butyl lithium, potassium hydride, etc. This salt formation generally is carried out at low temperatures i.e. from about −80° C. to −20° C., with temperatures of from −70° C. to −50° C. being preferred. In carrying out this salt formation any conventional inert organic solvent liquid at the aforementioned reaction temperatures can be utilized. The preferred solvents are the ether solvents such as tetrahydrofuran and dimethoxyethane.

After formation of the salt of the formula IV, the anionic form of the compound of formula IV is condensed with the compound of formula (III) to form the compound of formula V. This condensation is carried out utilizing the same solvents as used in the formation of the salt. In fact, it is preferred to carry out this reaction in the same reaction medium utilized to form the salt. In this regard, the compound of formula V can be formed by first adding the base to compound of formula IV followed thereafter by addition of the compound of formula III. The reaction of this salt with the compound of formula III to form the compound of formula V can be carried out at a higher temperature such as room temperature. However, poor yields of this compound of formula V are achieved at these higher temperature. Therefore, it is preferred to utilize low temperatures of i.e. from $-70°$ C. to $-50°$ C. in carrying out this reaction.

Where $R_1$ is fluorine in the compound of formula III this compound which has the formula:

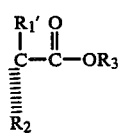   III-A wherein $R_1'$ is fluorine and $R_2$ and $R_3$ are as above can be prepared by fluorinating a compound of the formula

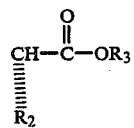   VI where $R_2$ and $R_3$ are above.

Any conventional method of fluorination can be utilized to convert the compound of formula VI to a compound of formula III-A. Among the preferred methods are utilizing a fluorinating agents such as perchlorofluoride, xenon difluoride or fluorine gas. Any of the conditions conventionally used with these types of fluorinating agents can be employed in this reaction.

After formation of the compound of formula V, the compound of formula V is converted to the compound of the formula:

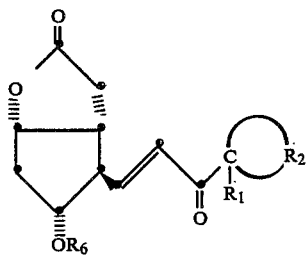   VII wherein $R_1$ and $R_2$ are as above; and $R_6$ taken together with its attached oxygen atom forms an ether or ester hydroxy protecting group by reaction with a compound of the formula:

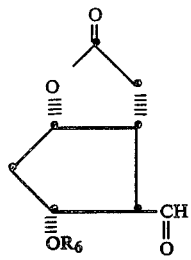   VIII wherein $R_6$ is as above.

The reaction of the compound of formula V with the compound of formula VIII to form the compound of formula VII is carried out by a Horner reaction. Any of the conditions conventional in carrying out Horner reactions can be utilized in carrying out the formation of compound of formula VII.

The compound of formula VII can be reduced with an alklai metal borohydride to form a compound of the formula

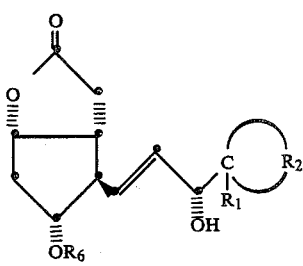   IX wherein $R_1$, $R_2$ and $R_6$ are as above in admixture with a compound of the formula

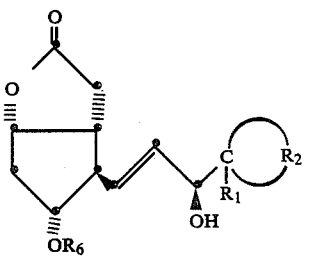   IX-A wherein $R_1$, $R_2$ and $R_6$ are as above. In carrying out this reaction, any of the conditions conventional in alkali metal borohydride reduction can be used. The compound of formula IX can be separated from the compound of formula IX-A by conventional means such as chromatography.

If desired, the compound of formula IX can be converted to the saturated compound of the formula:

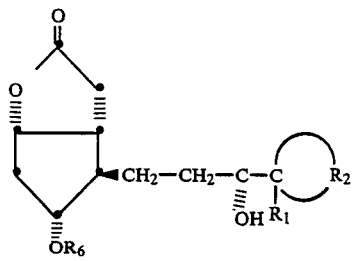

X wherein $R_2$, $R_3$ and $R_6$ are as above; by hydrogenation utilizing conventional hydrogenation catalysts such as palladium, rhodium and platinum. In carrying out this reaction any of the conditions conventionally used in catalytic hydrogenation can be used. If desired, this reaction can be carried out with $R_6$ being hydrogen as will be described hereinafter.

In the next step in the production of the compounds of formula I-A and I-B, the compounds of formula IX or X where $R_6$ is other than a tri(lower alkyl and/or aryl) silyl protecting group is converted to compounds of the formula

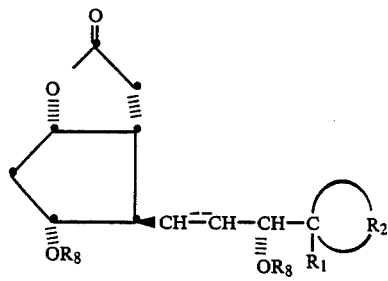

XI wherein $R_8$ is tri(lower alkyl and/or aryl)silyl; $R_1$ and $R_2$ are as above and the dotted bond can be optionally hydrogenated.

Where $R_6$ in the compounds of IX and X is an ether or ester protecting group other than a tri(lower alkyl and/or aryl)silyl protecting group, the compounds of formula IX and X can be converted to the compound of formula XI by first removal of the protecting group and then reaction with a tri(lower alkyl and/or aryl) halosilane, preferably t-butyl-dimethyl chlorosilane. Any of the conditions conventional in reacting a hydroxy compound with a halosilane to form a siloxy derivative can be used in carrying out this reaction. Where in the compounds of formula XI and X, $R_6$ is a cleavable either protecting group other than a tri(lower alkyl and/or aryl)silyl group, the protecting group can be removed by procedures well known in the art to produce a compound of the formula IX or X where $R_6$ is hydrogen. On the other hand, where $R_6$ is a hydrolyzable ester group, this group can be hydrolyzed by conventional means to form compounds of formula IX or X where $R_6$ is hydrogen. These latter compounds can be converted to the compound of formula XI by reaction with a tri(lower alkyl and/or aryl)halosilane as described above. The hydrogenation procedure described in preparing the compound of formula X can, if desired be utilized to reduce the double bond in the compounds of formula IX above where $R_6$ is hydrolyzed or cleaved to hydroxy group.

The compounds of formulae I and II are prepared from the compound of formula XI via the following intermediates:

XII

XIII

XIV

XV

XVI

XVII

-continued

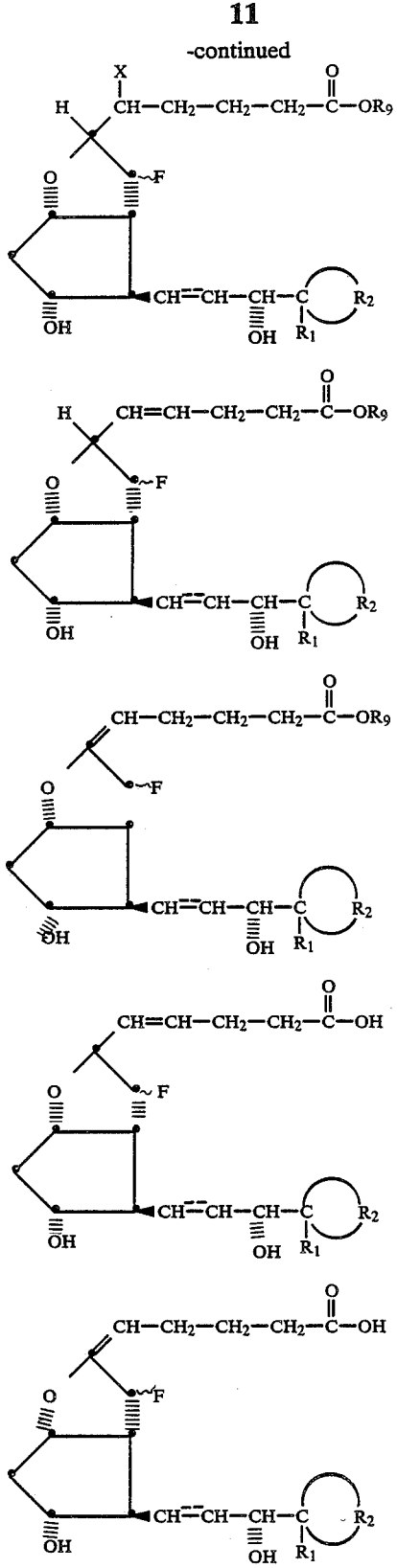

wherein $R_2$ and $R_8$ are as above; $R_9$ is lower alkyl and X is halogen; and $R_7$ is tri(lower alkyl and/or aryl)silyl and the dotted bond can be optionally hydrogenated.

The compound of formula XI is converted to the compound of formula XII by first enolizing the compound of formula XI and then treating the enolized form of the compound of formula XI with a tri(alkyl and/or aryl)halosilane. Any conventional method of enolizing can be utilized to enolize the compound of formula XI. Among the preferred methods is by treating the compound of formula XI with a non-aqueous alkali metal base. The preferred base for use in this reaction is lithium diisopropyl amide as well as sodium or lithium hexamethyldisilazane. In carrying out this reaction utilizing the non-aqueous alkali metal base, temperatures of $-70°$ C. to $30°$ C. are generally preferred. Generally, this reaction is carried out in an inert organic solvent. Any conventional inert organic solvent which is a liquid at the aforementioned temperatures can be utilized. Among the preferred solvents are tetrahydrofuran. The enolate of the compound of formula XI in the form of its alkali metal salt is converted to the compound of formula XII by treating with a tri(alkyl and/or aryl)halosilane, preferably trimethylchlorosilane. Generally, this reaction is carried out at the same temperatures and in the same solvent utilized to form the enolate.

The compound of formula XII is converted to the compound of formula XIII by treating the compound of formula XII with a fluorinating agent. Any conventional fluorinating agent can be utilized in carrying out this reaction. Among the preferred fluorinating agents is xenon difluoride. Generally, this reaction is carried out in the presence of an inert organic solvent. Any conventional inert organic solvent can be utilized in carrying out this reaction. Among the preferred solvents are halogenated hydrocarbons such as methylene chloride, carbon tetrachloride, etc. In carrying out this reaction, temperature and pressure are not critical and this reaction can be carried out at room temperature and atmospheric pressure. While room temperature can be utilized, it is preferred to carry out this reaction at low temperatures, i.e. from $-10°$ C. to $+10°$ C.

In converting the compound of formula XIII to the compound of formula XIV, the compound of formula XIII is produced as a mixture of the following compounds:

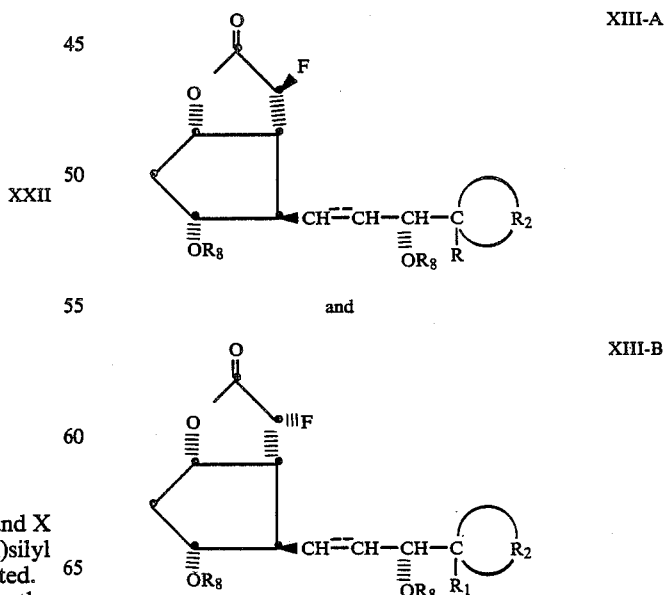

wherein $R_1$, $R_2$ and $R_8$ are as above.

The compounds of formulae XIII-A and XIII-B can be separated by conventional methods such as chromatography. On the other hand, the compound of formula XIII as a mixture of the compounds of formulae XIII-A and XIII-B can be utilized throughout the rest of the reactions or, if desired, separated at some later state in the reaction scheme to produce the compound of formulae I or II having whichever fluoro orientation is desired at the 7-position. If the compound of formula XIII is separated into the compound of formulae XIII-A and XIII-B, the same configuration of the 7-fluoro substituent is carried out throughout the rest of the reactions in producing the compounds of formula I or II. Therefore, in producing the compounds of formulae I or II wherein the fluoro substituent is in the 7-beta position, the compound of formula XIII-A is utilized in the rest of the reaction scheme to produce compounds of the formulae XIV through XXII wherein the 7-fluoro substituent in these formulae is in the beta position. If the compounds of formula I and II are desired wherein the fluoro substituent is in the 7-alpha position, then the compound of formula XIII-B is utilized in the reaction scheme to produce the compounds of formulae XIV through XXII wherein the fluoro substituent shown in these formulae is in the alpha position.

On the other hand, the compound of formula XIII can be utilized without separating into the compounds of formulae XIII-A and XIII-B. In this manner, the compounds of formulae I and II wherein the 7-fluoro substituent is in both the alpha and beta positions is produced via intermediates of the formulae XIV through XXII having the 7-fluoro group as shown.

The compound of formula XIII is converted to the compound of formula XIV by treating the compound of formula XIII with a reducing agent. In carrying out this reaction, any conventional reducing agent which will selectively reduce a lactone to a lactol can be utilized. Preferred reducing agents are the hydride reducing agents, particularly the aluminum hydrides such as alkyl aluminum hydrides and alkyl borohydrides. The preferred reducing agent is diisobutyl aluminum hydride. Also, this reaction can be carried out utilizing di(-branched chain lower alkyl)boranes such as bis(3-methyl-2-butyl)borane. In carrying out this reaction, temperature and pressure are not critical and the reaction can be carried out at room temperature and atmospheric pressure or reduced temperatures and pressures. Generally, it is preferred to carry out this reaction at a temperature of from $-80°$ C. to room temperature. This reduction reaction can be carried out in the presence of an inert organic solvent. Any of the conventional inert organic solvents can be utilized in carrying out this reaction. Among the preferred solvents are dimethoxy ethane and the ethers such as tetrahydrofuran, diethyl ether and dioxane.

The compound of formula XV is obtained from the compound of formula XIV by reaction the compound of formula XIV with phosphonium salts of the formula:

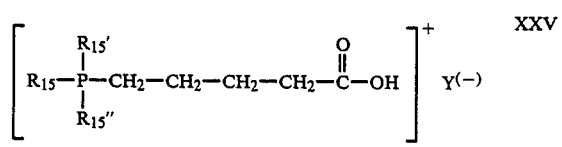

wherein $R_{15}$, $R_{15}'$, $R_{15}''$ are aryl or di(lower alkyl)-amino; and Y is halogen via a conventional Wittig type reaction. Any of the conditions conventional in Wittig reactions can be utilized in carrying out this reaction. However, it is generally preferred to utilize a small amount of an polar solvent such as hexamethylphosphoramide in this reaction mixture that undergoes this Wittig reaction.

The compound of formula XV can be converted to a compound of the formula XVI by esterification with diazomethane or a reactive derivative of a lower alkanol such as a lower alkyl halide. Any of the conditions conventionally utilized in these esterifying reactions can be utilized to form the compound of formula XVI from the compound of formula XV.

The compound of formula XVI is converted to the compound of formula XVII by treating the compound of formula XVI with a halogenating agent. Among the preferred halogenating agents are included N-halosuccinimides and halogen, particularly N-iodosuccinimide and iodine. Generally, this reaction is carried out in the presence of a polar solvent such as acetonitrile and halogenated hydrocarbons such as methylene chloride, ethylene chloride, etc. In fact, any conventional polar organic solvent can be utilized. In carrying out this reaction, temperatures of from 0° C. to 35° C. can be utilized. Generally, it is preferred to carry out this reaction at room temperature.

The compound of formula XVII is converted to the compound of formula XVIII by ether cleavage. Any conventional method of ether cleavage can be utilized to carry out this reaction.

In the next step, the compound of formula XVIII is treated with a dehydrohalogenating agent to produce the compounds of formulae XIX and XX in admixture. In carrying out this reaction, any conventional dehydrohalogenating agent can be utilized. Among the preferred dehydrohalogenating agents are the diazabicycloalkanes or alkanes such as 1,8-diazabicyclo[5.4.0]undec-7-ene and 1,4-diazabicyclo[2.2.2]octane. Furthermore, any other conventional organic base utilized for dehydrohalogenation can be utilized in carrying out this reaction. This reaction produces the compounds of formula XIX and the compounds of formula XX in admixture. The compounds of formula XIX can be separated from the compounds of formula XX by any conventional separation procedure such as chromatography.

The compound of formula XIX can be converted to the compound of formula XXI and the compound of formula XX can be converted to the compound of formula XXII by hydrolysis. Any conventional method of ester hydrolysis can be utilized in carrying out these reactions. Among the preferred method of ester hydrolysis is either treating the compound of formula XIX or the compound of formula XXV with a alkali metal hydroxide. Among the preferred alkali metal hydroxides for use in this reaction are sodium and potassium hydroxides. This hydrolysis produces the compound of formula XXII in its salt form.

In producing the compound of formula I and II where $R_5$ is lower alkanoyl, the compounds of formulae XIX, XX, XXI and XXII are esterified with a lower alkanoic acid or reactive derivative thereof such as halide or anhydride of a lower alkanoic acid. Any of the conventional means utilized for esterification with a lower alkanol acid, or reactive derivatives thereof can be utilized to carry out this conversion. The preferred lower alkanoyl group is acetyl.

In the practice of this invention, any pharmaceutically acceptable basic salts of the compound of formula I and II where R is hydrogen can be utilized. Among the preferred pharmaceutically acceptable basic salts are included the alkali metal salts such as lithium, sodium, and potassium, with sodium being especially preferred. Other salts which are also preferred are the alkaline earth metal salts such as calcium and magnesium, amine salts such as the lower alkyl amines, e.g. ethylamine and the hydroxy-substituted lower alkyl amine salts and tris(hydroxymethyl)amino-methane. Also preferred are the ammonium salts. Among the other salts are dibenzylamine, monoalkylamines or dialkylamine and salts with amino acids (i.e. salts with arginine and glycine).

The following Examples are illustrative but not limitative of the invention. In the Examples, the ether utilized was diethyl ether. All temperatures are in degrees Centigrade. Celite is diatomaceous earth and DMF is dimethyl formamide.

EXAMPLE 1

[2-(1-Methylcyclohexyl)-2-oxoethyl]phosphonic acid, dimethyl ester

To a solution of 75.64 g dimethyl methyl phosphonate in 380 ml tetrahydrofuran, under argon atmosphere and cooled by a dry ice/acetone bath, was added 380 ml of 1.6M n-butyllithium solution in hexane. After being stirred at −78° C. for 1.5 hrs, a solution of 47.1 g ethyl 1-methylcyclohexanecarboxylate in 100 ml tetrahydrofuran was added through an addition funnel over 15 min. The resulting solution was stirred at −78° C. for 4.5 hrs. after which 100 ml of 3N H₂SO₄ solution was added and the mixture stirred at room temperature for 10 min and then transferred to a separatory funnel. An additional 100 ml 3N H₂SO₄ solution was added and the aqueous layer was extracted three times with ether (3×100 ml). The combined organic extracts were washed once with 100 ml brine solution, dried over MgSO₄ and concentrated under reduced pressure. The crude oily product was distilled to give 53.64 g of [2-(1-methylcyclohexyl)-2-oxoethyl]-phosphonic acid dimethyl ester as colorless liquid, b.p. 128°–134° C./0.7 mmHg.

Calc.: C, 53.22; H, 8.53; P, 12.48. Found: C, 52.98; H, 8.50; P, 12.23.

EXAMPLE 2

[3aR-[3a alpha,4alpha(1E),5beta,6a alpha]]-5-(Benzoyloxy)=hexahydro-4-[3-(1-methylcyclohexyl)-3-oxo-1-propenyl]-2H-cyclopenta[b]furan-2-one To a suspension of 1.70 g sodium hydride (50% by weight oil suspension) in 30 ml tetrahydrofuran cooled with an ice bath was added a solution of 8.76 g dimethyl[2-(1-methylcyclohexyl)-2-oxoethyl]phosphonate in 70 ml tetrahydrofuran. After 2 hrs., a solution of 8.38 g [3aR-[3a alpha,4alpha,5beta,6a alpha]]-5-(benzoyloxy)-hexahydro-4-formyl-2H-cyclopenta[b]furan-2-one in 150 ml tetrahydrofuran was added and the resulting mixture was stirred for 3 hrs. 100 ml of 1N HCl was then added to quench the reaction. The mixture was transferred to a separatory funnel and extracted three times with ether (100 ml). The combined organic layers were washed once with 60 ml of brine, dried over MgSO₄ and concentrated under reduced pressure. The crude product thus obtained was purified by crystallization from ethanol to yield 9.66 g of [3aR-[3a alpha,4alpha(1E),5beta,6a alpha]]-5-(benzoyloxy)hexahydro-4-[3-(1-methylcyclohexyl)-3-oxo-1-propenyl]-2H-cyclopenta[b]furan-2-one as a white solid; m.p. 107°–108° C.

Calc.: C, 72.71; H, 7.12. Found: C, 71.99; H, 7.27.

EXAMPLE 3

[3aR-[3a alpha,4alpha(1E,3R*),5beta,6a alpha]]-5-(Benzoyloxy)hexahydro-4-[3-hydroxy-3-(1-methylcyclohexyl)-1-propenyl]-2H-cyclopenta[b]furan-2-one To a solution of 5.4 g of [3aR-[3a alpha,4alpha(1E),5beta, 6alpha]]-5-(benzoyloxy)hexahydro-4-[3-(1-methylcyclohexyl)-3-oxo-1-propenyl]-2H-cyclopenta[b]furan-2-one in 70 ml methanol and 70 ml tetrahydrofuran, cooled with an ice bath, was added 0.56 g of sodium borohydride in one portion. The resulting mixture was stirred at ice bath temperature for 1.5 hrs and then quenched with 50 m of 1N HCl. After 30 min @ 0° C. most of the organic solvents were removed under aspirator pressure and the residue was extracted with ethyl acetate (3×100 ml). The combined ethyl acetate extracts were washed once with 50 ml brine solution, dried over MgSO₄, and concentrated under reduced pressure. The crude product thus obtained was further purified by chromatography using Waters Prep 500 Columns. Elution with toluene/ethyl acetate (3:1) gave 2.75 g (6.90 mmole) of [3aR-[3a alpha,4alpha(1E,3R*),-5beta,6a alpha]]-5-(benzoyloxy)hexahydro-4-[3-hydroxy-3-(1-methylcyclohexyl)-1-propenyl]-2H-cyclopenta[b]furan-2-one as a white solid, m.p. 83.5°–85.0° C.

Calc.: C, 72.34; H, 7.59. Found: C, 72.41; H, 7.65.

Further elution afforded 2.40 g (6.02 mmole) of the 15beta isomer, i.e. [3aR-[3a alpha,4alpha(1E,3S*),-5beta,6a alpha]]-5-(benzoyloxy)hexahydro-4-[3-hydroxy-3-(1-methylcyclohexyl)-1-propenyl]-2H-cyclopenta[b]furan-2-one.

EXAMPLE 4

[3aR-[3a alpha,4alpha(1E,3R*),5beta,6a alpha]]-Hexahydro-5-hydroxy-4-[3-hydroxy-3-(1-methylcyclohexyl)-1-propenyl]-2H-cyclopenta[b]furan-2-one To a solution of 2.9 g of [3aR-[3a alpha,4alpha(-1E,3R*), 5beta,6a alpha]]-5-(benzoyloxy)hexahydro-4-[3-hydroxy-3-(1-methylcyclohexyl)-1-propenyl]-2H-cyclopenta[b]furan-2-one in 100 ml methanol was added 2 g of sodium carbonate and the resulting mixture stirred at room temperature overnight. The mixture was filtered and 1 ml of glacial acetic acid was added to the filtrate. After concentration under reduced pressure, the crude product was purified by flash chromatography on 200 g of silica gel (eluting with ethyl acetate) to give 2.06 g of [3aR-[3a alpha, 4alpha(1E,3R*),5beta,6a alpha]]-hexahydro-5-hydroxy-4-[3-hydroxy-3-(1-methylcyclohexyl)-1-propenyl]-2H-cyclopenta[b]furan-2-one as a white solid: m.p. 139°–140° C.

Calc.: C, 69.36; H, 8.90. Found: C, 68.97; H, 8.73.

EXAMPLE 5

[3aR-[3a alpha,4alpha(1E,3R*),5beta,6a alpha]]-Hexahydro-5-[[(1,1-dimethylethyl)dimethylsilyl]oxy]-4-[3-[[(1,1-dimethylethyl)dimethylsilyl]oxy]-3-(1-methylcyclohexyl)-1-propenyl]-2H-cyclopenta[b]furan-2-one To a solution of 2.06 g of [3aR-[3a alpha,4 alpha (1E,3R*),5beta,6a alpha]]-hexahydro-5-hydroxy-4-[3-hydroxy-3-(1-methylcyclo-hexyl)-1-propenyl]-2H-cyclopenta[b]furan-2-one in 56 ml of dimethylformamide was added 2.8 g of imidazole followed by 4.9 g of t-butyldimethyl-silyl chloride. The resulting solution was stirred at room temperature overnight; poured into 300 ml of 0.5N HCl, and extracted with ether (3×250 ml). The combined ethereal layers were washed successively with 50 ml of saturated NaHCO$_3$ solution, 50 ml of brine and 100 ml of water. The ether layer was then dried (MgSO$_4$) and concentrated under reduced pressure. The residual material was chromatographed on 200 g of silica gel, eluting first with hexane (2 L), followed by 8% (v/v) ethyl acetate in hexane to give 3.58 g of [3aR-[3a alpha, 4alpha(1E,3R*),5beta,6a alpha]]-hexahydro-5-[[(1,1-dimethylethyl)dimethylsilyl]oxy]-4-[3-[[(1,1-dimethyethyl)dimethylsilyl]oxy]-3-(1-methylcyclohexyl)-1-propenyl]-2H-cyclopenta[b]furan-2-one as a white solid m.p. 136°–137° C.

Calc.: C, 66.61; H, 10.41; Si, 10.73. Found: C, 66.34; H, 10.46; Si, 10.90.

EXAMPLE 6

[3S-[3alpha,3a alpha,4alpha(1E,3R*),5beta,6a alpha]]-4-[3-[[(1,1-Dimethylethyl)dimethylsilyl]oxy]-3-(1-methylcyclohexyl)-1-propenyl]-5-[[(1,1-dimethylethyl)dimethylsilyl]oxy]-3-fluorohexahydro-2H-cyclopenta[b]furan-2-one To a solution of 3.26 g of [3aR-[3a alpha,4alpha(-1E,3R*), 5beta,6a alpha]]-hexahydro-5-[[(1,1-dimethylethyl)=dimethylsilyl]oxy]-4-[3-[[(1,1-dimethylethyl)dimethylsilyl]oxy]-3-(1-methylcyhclohexyl)-1-propenyl]-2H-cyclopenta[b]furan-2-one in 40 ml tetrahydrofuran (kept under an argon atmosphere and cooled at −78° C.) was added a solution of 2.00 g of lithium hexamethyldisilazide in 30 ml of tetrahydrofuran. The resulting solution was stirred for 70 min. When the temperature of the cold bath rose to −25° C. 3.0 ml of trimethylsilyl chloride was added through a syringe. The cold bath was removed and the resulting mixture stirred for 1 hr. Solvents and excess reagents were removed under aspirator pressure and the residue was further dried for 3 hrs. on a vacuum pump. At this point 60 ml of dried methylene chloride was added to the residue which was again kept under an argon atmosphere and cooled to −10° C. with an acetone/dry ice bath. A mixture of 1.53 g of potassium bicarbonate and 2.31 g of xenon difluoride was added in one portion. The resulting mixture was stirred for 15 min after which a solution of 5 g of sodium thiosulfate in 100 ml saturated NaHCO$_3$ solution was added to quench the reaction and stirring was continued for 10 min. The mixture was transferred to a separatory funnel, another 100 ml of the above-mentioned Na$_2$S$_2$O$_3$ solution was added and the mixture extracted three times with ether (2×10 ml). The ethereal extracts were combined, washed once with 70 ml of saturated NaHCO$_3$ solution, once with 70 ml of brine, dried over MgSO$_4$ and concentrated under reduced pressure. The crude product was purified by flash chromatography on 550 g of silica gel. Elution with hexane/ethyl acetate (20-1) afforded 1.71 g of [3S-[3alpha,3a alpha, 4alpha(1E,3R*),5beta,6a alph a]]-4-[3-[[(1,1-dimethylethyl)dimethylsilyl]oxy]-3-(1-methylcyclohexyl)-1-propenyl]-5-[[(1,1-dimethylethyl)-dimethylsilyl]oxy]-3-fluoro-hexahydro-2H-cyclopenta[b]furan-2-one as a white solid, m.p. 102°–104° C.

Calc.: C, 64.40; H, 9.88; F, 3.51; Si, 10.38. Found: C, 63.96; H, 9.83; F, 3.77; Si, 10.18.

EXAMPLE 7

3S-[3alpha,3a alpha,4alpha(1E,3R*),5beta,6a alpha]]-4-[3-[[(1,1-Dimethylethyl)-dimethylsilyl]oxy]-3-(1-methylcyclohexyl)-1-propenyl]-5-[[(1,1-dimethylethyl)-dimethylsilyl]oxy]-3-fluoro-hexahydro-2H-cyclopenta[b]furan-2-ol To a solution of 1.65 g (3.05 mmole) [3S-[3alpha,3a alpha, 4alpha(1E,3R*),5beta,6a alpha]]-4-[3-[[(1,1-dimethylethyl)dimethylsilyl]oxy]-3-(1-methylcyclohexyl)-1-propenyl]-5-[[(1,1-dimethylethyl)dimethylsilyl]oxy]-3-fluorohexahydro-2H-cyclopenta[b]furan-2-one in 25 ml of toluene, kept under an argon atmosphere and cooled at −78° C., was added 4.1 ml of a solution of diisobutylaluminum hydride in toluene (1.5M).

After 30 min at −78° C., 60 ml of 1N HCl was added and the mixture extracted with ether (2×100 ml), then once with 100 ml of ethyl acetate. The combined organic layers were washed once with 60 ml of 1N HCl and 60 ml of brine, dried (MgSO$_4$) and concentrated under reduced pressure. The crude product was purified by flash chromatography on 100 g of silica gel, eluting with hexane/ethyl acetate, to afford 1.278 g of [3S-[3alpha,3a alpha,4alpha(1E,3R*), 5beta,6a alpha]]-4-[3-[[(1,1-dimethylethyl)dimethylsilyl]oxy]-3-(1-methylcyclohexyl)-1-propenyl]-5-[[1,1-dimethylethyl)-dimethylsilyl]oxy]-3-fluorohexahydro-2H-cyclopenta[b]furan-2-ol as a colorless oil.

EXAMPLE 8

[1S-[1alpha(1R*,2Z),2beta(1E,3R*),3alpha,5alpha]]--7-[2-[3-(1-methylcyclohexyl)-3-[[(1,1-dimethylethyl)-dimethylsilyl]oxy]-1-propenyl]-3-[[(1,1-dimethylethyl)-dimethylsilyl]oxy]-5-hydroxycyclopentyl]-7-fluoro-5-heptenoic acid methyl ester To a suspension of 2.7 g (4-carboxybutyl)triphenylphosphonium bromide in 20 ml of tetrahydrofuran under an argon atmosphere was added 2.23 g of sodium hexamethyldisilazide. The resulting orange-red mixture was stirred at room temperature for 10 min and then heated in an oil bath (bath temperature 47° C.) for 2 hrs. The flask was revoved from the oil bath and a solution of 657.6 mg of [3S-[3alpha,3a alpha, 4alpha(1E,3R*),-5beta,6a alpha]]-4-[3-[[(1,1-dimethylethyl)dimethylsilyl]oxy]-3-(1-methylcyclohexyl)-1-propenyl]-5-[[(1,1-dimethylethyl)dimethylsilyl]oxy]-3-fluorohexahydro-2H-cyclopenta[b]furan-2-ol in 16 ml of tetrahydrofuran was added. The resulting mixture was allowed to stir overnight after which 60 ml of ice cold 1N HCl was added and the resulting mixture was extracted with ether (3×100 ml). The combined ethereal extracts were washed once with 60 ml of 1N HCl, once with 60 ml of brine, dried (MgSO$_4$) and concentrated under reduced pressure. The residue was dissolved in 20 ml of ether, cooled with an ice bath, and treated with excess ethereal diazomethane solution. The solvent and excess reagent was removed under reduced pressure and the residue purified by flash chromatography on 100 g of silica gel.

Elution with hexane/ethyl acetate (8:1 v/v) afforded 647 mg of [1S-[1alpha(1R*,2Z),2beta (1E,3R*),3alpha,5alpha]]-7-[2-[3-(1-methylcyclohexyl)-3-[[(1,1-dimethylethyl)dimethylsilyl]oxy]-1-propenyl[-3-[[(1,1-dimethyl-ethyl)dimethylsilyl]oxy]-5-hydroxycyclopentyl]-7-fluoro-5-heptenoic acid methyl esther as a light yellow oil.

Calc.: C, 65.58; H, 10.22; F, 2.96; Si, 8.76. Found: C, 65.42; H, 10.17; F, 3.09; Si, 8.62.

EXAMPLE 9

[2R-[2beta(R*),3beta,3a beta,4beta(1E,3R*),5alpha,6a beta]]-3-Fluorohexahydro-5-[[(1,1-dimethylethyl)-dimethyl silyl]oxy]-4-[3-[[(1,1-dimethylethyl)dimethylsilyl]oxy]-3-(1-methylcyclohexyl)-1-propenyl]-delta-iodo-2H-cyclopenta[b]-furan-2-pentanoic acid methyl ester and

[2S-[2alpha(S*),3beta,3a beta,4beta(1E,3R*),5alpha,6a beta]]-3-Fluorohexahydro-5-[[(1,1-dimethylethyl)dimethylsilyl]oxy]-4-[3-[[(1,1-dimethylethyl)dimethylsilyl]oxy]-3-(1-methylcyclohexyl)-1-propenyl]-delta-iodo-2H-cyclopenta[b]furan-2-pentanoic acid methyl ester To a solution of 412.3 mg of [1S-[1alpha(1R*,2Z),-2beta (1E,3R*),3alpha,5alpha]]-7-[2-[3-(1-methylcyclohexyl)-3-[[(1,1-dimethylethyl)dimethylsilyl]oxy]-1-propenyl]-3-[[(1,1-dimethylethyl)dimethylsilyl]oxy]-5-hydroxycyclopentyl]-7-fluoro-5-heptenoic acid methyl ester in 12 ml acetonitrile was added 0.75 g of N-iodosuccinimide. The resulting mixture was stirred at room temperature for 18 hrs. and then transferred to a separatory funnel. 200 ml of ether was added and the solution washed with an aqueous solution prepared by dissolving 3 g of sodium bisulfite in 60 ml of water (2×30 ml), once with 30 ml of saturated sodium bicarbonate solution and once with 30 ml of brine. After drying (MgSO4) the solution was concentrated under reduced pressure. The crude product thus obtained was purified by flash chromatography on 100 g of silica gel. Elution with hexane/ethyl acetate (24:1 v/v), afforded 242.5 mg of [2R-[2beta(R*),3beta,3a beta,4beta(-1E,3R*),5alpha,6a beta]]-3-fluorohexahydro-5-[[(1,1-dimethylethyl)dimethylsilyl]oxy]-4-[3-[[(1,1-dimethylethyl)dimethylsilyl]oxy]-3-(1-methylcyclohexyl)-1-propenyl]-delta-iodo-2H-cyclopenta[b]furan-2-pentanoic acid methyl ester as a colorless oil.

Further elution afforded 52.7 mg of [2S-[2alpha(S*),-3beta, 3a beta,4beta(1E,3R*),5alpha,6a beta]]-3-fluorohexahydro-5-[[(1,1-dimethylethyl)dimethylsilyl]oxy]-4-[3-[[(1,1-dimethylethyl)dimethylsilyl]oxy]-3-(1-methylcyclohexyl)-1-propenyl]-delta-iodo-2H-cyclopenta[b]furan-2-pentanoic acid methylester, also as a colorless oil

EXAMPLE 10

[3S-[3alpha,3a alpha,4alpha(1E,3R*),5beta,6a alpha]]-3-Fluorohexahydro-5-hydroxy-4-[3-hydroxy-3-(1-methylcyclohexyl)-1-propenyl]-delta-iodol-2H-cyclopenta[b]furan-2-pentanoic acid methyl ester A 997.3 mg mixture of crude product obtained as described in Example 9 containing [2R-[2beta(R*),-3beta,3a beta,4beta (1E,3R*),5alpha,6a beta]]-3-fluorohexahydro-5-[[(1,1-dimethyl-ethyl)dimethylsilyl]oxy]-4-[3-[[(1,1-dimethylethyl)dimethylsilyl]oxy]-3-(1-methylcyclohexyl)-1-propenyl]-delta-iodo-2H-cyclopenta [b]furan-2-pentanoic acid methyl ester and [2S-[2alpha(S*), 3beta,3a beta,4beta(1E,3R*),5alpha,6a beta]]-3-fluorohexahydro-5-[[(1,1-dimethylethyl)dimethylsilyl]oxy]-4-[3-[[(1,1-dimethylethyl)dimethylsilyl]oxy]-3-(1-methylcyclohexyl)-1-propenyl]-delta-iodo-2H-cyclopenta[b]furan-2-pentanoic acid methyl ester was dissolved in 12 ml of tetrahydrofuran. To this was added 8 ml of H2O and 16 ml of glacial acetic acid. The mixture was heated in an oil bath kept at 60° C. for 7 days. After being cooled to room temperature, the mixture was transferred to a separatory funnel and diluted with 360 ml ethyl acetate, washed with saturated sodium bicarbonate solution (6×50 ml), once with 50 ml of brine, dried (MgSO4) and concentrated under reduced pressure. The crude product was purified by flash chromatography on 50 g of silica gel using ethyl acetate as the eluent to yield 301 mg of [3S-[3alpha,3aalpha,4alpha (1E,3R*),5beta,6aalpha]]-3-fluorohexahydro-5-hydroxy-4-[3-hydroxy-3-(1-methylcyclohexyl)-1-propenyl]-delta-iodo-2H-cyclopenta[b]furan-2-pentanoic acid methyl ester as a colorless oil

EXAMPLE 11

[3S-[(Z),3alpha,3a alpha,4alpha(1E,3R*),5beta,6a alpha]]]-5-[3-Fluorohexahydro-5-hydroxy-4-[3-hydroxy-3-(1-methylcyclohexyl)-1-propenyl]-2H-cyclopenta[b]furan-2-ylidene]pentanoic acid methyl ester and

[2S-[2alpha(4E),3alpha,3a alpha,4alpha(1E,3R*),5beta,6a alpha]]-5-[3-fluorohexahydro-5-hydroxy-4-[3-hydroxy-3-(1-methylcyclo=hexyl)-1-propenyl]-2H-cyclopenta[b]furan-2-yl]-4-pentenoic acid methyl ester To a solution of 194.3 mg of [3S-[3alpha, 3a alpha,4alpha(1E,3R*),5beta,6a alpha]]-3-fluorohexahydro-5-hydroxy-4-[3-hydroxy-3-(1-methylcyclohexyl)-1-propenyl]delta-iodo-2H-cyclopenta[b]furan-2-pentanoic acid methyl ester in 5 ml of toluene was added 0.4 ml of 1.8-diazabicyclo [5.4.0] dec-7-ene. The resulting solution was heated in a oil bath kept at 90° C. for 64 hrs. After being cooled to room temperature, most of the solvent was removed under reduced pressure, and the residue was directly purified by flash chromatography on 20 g of silica gel. Elution with ethyl acetate/toluene (3:1, v/v) containing triethylamine (0.5% by volume) afforded 79.5 mg of [3S-[(Z),3alpha,3a alpha,4alpha(1E,3R*),5beta,6a alpha]]-5-[3-fluorohexahydro-5-hydroxy-4-[3-fluorohexahydrod-5-hydroxy-4-[3-hydroxy-3-(1-methylcyclohexyl)-1-propenyl]-2H-cyclopenta[b]furan-2-ylidene]pentanoic acid methyl ester as a colorless oil. Further elution afforded 25.4 mg of [2S-[2alpha(4E),3alpha,3a alpha,4alpha(1E,3R*),-5beta,6a alpha]]-5-[3-fluorohexahydro-5-hydroxy-4-[3-hydroxy-3-(1-methylcyclohexyl)-1-propenyl]-2H-cyclopenta[b]furan-2-yl]-4-pentenoic acid methyl ester also as a colorless oil.

EXAMPLE 12

[3S-[(Z),3alpha,3a alpha, 4alpha(1E,3R*),5beta,6a alpha]]-5-[3-Fluorohexahydro-5-hydroxy-4-[3-hydroxy-3-(1-methylcyclohexyl)-1-propenyl]-2H-cyclopenta[b]furan-2-ylidene]pentanoic acid, sodium salt To a solution of 50.8 mg of [3S-[(Z),3alpha,3a alpha,-4alpha (1E,3R*),5beta,6a alpha]]-5-[3-fluorohexahydro-5-hydroxy-4-[3-hydroxy-3-(1-methylcyclohexyl)-1-propenyl]-2H-cyclopenta[b]-furan-2-ylidene]pentanoic acid methyl ester in 1 ml of tetrahydrofuran and 1 ml of methanol, there was added 0.621 ml of 0.2N NaOH solution. The resulting mixture was stirred at room temperature for 47 hrs. Solvents were then removed under reduced pressure and the residue was further dried on a vacuum pump for 2 hrs. A mixture of 3 ml of ethyl acetate and 40 drops of methanol was added to dissolve the residue. The solution was filtered through a small pad of cotton placed in a test tube. To the filtrate was added 10 ml of hexane and the cloudy mixture was placed in a freezer overnight. The supernatant solution was carefully transferred to an Erlenmeyer flask and enough ethyl ether was added to precipitate out the sodium salt. This mixture containing the precipitated was filtered through a small pad of cotton placed in a test tube. Then 10 ml of distilled water was used to dissolve the precipitate left in the flask and on the cotton. The water solution was chilled with dry ice and the solid mass was then lyophlyzed to give 31.4 mg of [3S-(Z),3alpha,3a alpha,4alpha(1E,3R*),5beta,6a alpha]]-5-[3-fluorohexahydro-5-hydroxy-4-[3-hydroxy-3-(1-methylcyclohexyl)-1-propenyl]-2H-cyclopenta[b]furan-2-ylidene]pentanoic acid, sodium salt as a hygroscopic solid.

EXAMPLE 13

1-Fluorocyclopentanecarboxylic acid, ethyl ester

To a solution of 17.6 ml of diisopropylamine in 100 ml of tetrahydrofuran, cooled at −78° C. and kept under an argon atmosphere, was added 75 ml of n-butyllithium solution in hexane (1.6M). The resulting solution was stirred at −78° C. for 25 min. A solution of 14.2 g of ethyl cyclopentanecarboxylate in 80 ml of tetrahydrofuran was added dropwise over a 70 min period. After being stirred at −78° C. for 3 hrs, this solution was transferred via a cannula to a solution of perchloryl fluoride in tetrahydrofuran (prepared by passing a stream of perchloryl fluoride in argon into 200 ml of tetrahydrofuran kept at −78° C. for 22 min.

The passage of perchloryl fluoride was continued during the transfer of the ester enolate solution and for another 11 min. after the transfer was complete. The excess perchloryl fluoride was then purged from the solution by passing argon through the solution for 30 min. 100 ml of saturated NH$_4$Cl solution was then added to quench the reaction and the resulting mixture was allowed to warm to room temperature. After partitioning, the separated aqueous layer was extracted with ether (2×100 ml). Most of the solvents from the organic layer were removed on a rotary evaporator and the residue dissolved in 200 ml ether. The ethereal solution was washed once with 100 ml of brine, dried (MgSO$_4$) and concentrated under reduced pressure.

A second batch was prepared from 17.76 g of ethyl cyclopentane carboxylate. The crude products from the two runs were combined and purified by distillation at reduced pressure to give 27.52 g of ethyl 1-fluorocyclopentanecarboxylate as colorless liquid; b.p. 108°–110° C. at 169 mm.

EXAMPLE 14

[2-(1-Fluorocyclopentyl)-2-oxoethyl]phosphonic acid, dimethyl ester

By the procedure of Example 1, 1-fluoro-cyclopentane=carboxylic acid ethyl ester was converted to [2-(1-fluorocyclopentyl)-2-oxoethyl]phosphonic acid dimethyl ester; bp 115°–118° at 0.12 mmHg.

Calc.: C, 45.38; H, 6.77; F, 7.98. Found: C, 45.13; H, 6.89; F, 7.08.

EXAMPLE 15

[3aR-[3a alpha,4alpha(1E),5beta,6a alpha]-5-(benzoyloxy)-4-[3-(1-fluorocyclopentyl)-3-oxo-1-propenyl]hexahydro-2H-cyclopenta[b]furan-2-one By the procedure of Example 2, [2-(1-fluorocyclopentyl)-2-oxoethyl)phosphonic acid dimethyl ester was condensed with [3aR-[3a alpha, 4alpha,5beta,6a alpha]]-5-(benzoyloxy)=hexahydro-4-formyl-2H-cyclopenta[b]furan-2-one to give [3aR-[3a alpha,4alpha(1E),5beta,6a alpha]]-5-(benzoyloxy)-4-[3-(1-fluorocyclopentyl)-3-oxo-1-propenyl]hexahydro-2H-cyclopenta[b]furan-2-one; mp 145°–6° C.

Calc.: C, 68.38; H, 6.00; F, 4.92. Found: C, 68.53; H, 6.03; F, 4.63.

EXAMPLE 16

[3aR-[3a alpha,4alpha(1E,3R*),5beta, 6a alpha]]-5-(benzoyloxy)-4-[3-(1-fluorocyclopentyl)-3-hydroxy-1-propenyl]hexahydro-2H-cyclopenta[b]furan-2-one By the procedure of Example 3 [3aR-[3a alpha, 4 alpha,(1E), 5 beta, 6a alpha]-5-(benzyloxy)-4-[3-(1-fluorocyclopentyl)-3-oxo-1-propenyl]hexahydro-2H-cyclopenta[b]furan-2-one was reduced to a mixture of allylic alcohols which upon silica gel chromatography was separated to give [3aR-[3a alpha,4alpha (1E,3R*),-5beta,6a alpha]]-5-(benzoyloxy)-4-[3-(1-fluorocyclopentyl)-3-hydroxy-1-propenyl]hexahydro-2H-cyclopenta[b]furan-2-one; mp 73°–4° C.

Calc. C, 65.01; H, 6.70; F, 4.67. Found: C, 65.03; H, 6.65; F, 4.91.

Continued elution yielded the 15β isomer [3aR-[3a alpha,4alpha(1E,3S*), 5beta, 6a alpha]]-5-(benzoyloxy)-4-[3-(1-fluorocyclopentyl)-3-hydroxy-1-propenyl]hexahydro-2H-cyclopenta[b]furan-2-one; mp 70°–2° C.

Calc. C, 65.01; H, 6.70; F, 4.67. Found C, 65.36; H, 6.54; F, 4.46.

EXAMPLE 17

[3aR-[3a alpha,4alpha(1E,3R*),5beta,6a alpha]]-4-[3-(1-Fluoro-cyclopentyl)-3-hydroxy-1-propenyl]hexahydro-5-hydroxy-2H-cyclopenta[b]furan-2-one By the procedure of Example 4, [3aR-[3a alpha,4alpha (1E,3R*),5beta,6a alpha]]-5-benzoyloxy)-4-[3-(1-fluorocyclopentyl)-3-hydroxy-1-propenyl]hexahydro-2H-cyclopenta[b]furan-2-one was converted to [3aR-[3a alpha,4alpha(1E,3R*), 5beta,6a alpha]]-4-[3-(1-fluorocyclopentyl)-3-hydroxy-1-propenyl]hexahydro-5-hydroxy-2H-cyclopenta[b]furan-2-one; mp 125°–7° C.

Calc.: C, 63.37; H, 7.44; F, 6.68. Found: C, 63.25; H, 7.47; F, 6.43.

EXAMPLE 18

[3aR-[3a alpha,4alpha(1E,3R*),5beta,6a alpha]]-4-[3-(1-Fluoro-cyclopentyl)-3-[[(1,1-dimethylethyl)-dimethylsilyl]oxy]-1-propenyl]-5-[[(1,1-dimethylethyl)-dimethylsilyl]oxy-hexahydro-2H-cyclo-penta[b]furan-2-one By the procedure of Example 5 [3aR-[3a alpha,4alpha, (1E,3R*)5beta, 6a alpha]]-4-[3-(1-fluorocyclopentyl)-3-hydroxy-1-propenyl]hexahydro-5-hydroxy-2H-cyclopenta[b]furan-2-one was converted to [3aR-[3a alpha,4alpha(1E,3R*), 5beta,6a alpha]]-4-[3-(1- fluorocyclopentyl)-3-[[(1,1-dimethylethyl)dimethyl-silyl]oxy]-1-propenyl]-5-[[(1,1-dimethylethyl)dimethyl-sil]oxy-hexahydro-2H-cyclopenta[b]furan-2-one

EXAMPLE 19

[3S-[3alpha,3a alpha,4alpha(1E,3R*),5beta,6a alpha]]-4-[3-(1-Fluorocyclopentyl)-3-[[(1,1-dimethylethyl)dimethylsilyl]oxy]-1-propenyl]-5-[[(1,1-dimethylethyl)dimethylsilyl]oxy]-3-fluoro-hexahydro-2H-cyclopenta[b]furan-2-one By the procedure of Example 6, [3aR-[3a alpha,4alpha (1E,3R*),5beta,6a alpha]]-4-[3-(1-fluorocyclopentyl)-3-[[(1,1-dimethylethyl)dimethylsilyl]oxy]-1-propenyl]-5-[[(1,1-dimethylethyl)dimethylsilyl]oxy]-hexahydro-2H-cyclopenta[b]furan-2-one was fluorinated to produce [3S-[3alpha,3a alpha,4alpha (1E,3R*),-5beta,6a alpha]]-4-[3-(1-fluorocyclopentyl)-3-[[(1,1-dimethylethyl)dimethylsilyl]oxy]-1-propenyl]-5-[[(1,1-dimethylethyl)silyl]oxy]-3-fluorohexahydro-2H-cyclopenta [b]furan-2-one Calc.: C, 61.09; H, 9.11; F, 7.16. Found: C, 61.20; H, 9.00; F, 7.18.

EXAMPLE 20

[3S-[3alpha,3a alpha,4alpha(1E,3R*),5beta,6a alpha]]-4-[3-(1-Fluorocyclopentyl)-3-[[(1,1-dimethylethyl)dimethylsilyl]oxy]-1-propenyl]-5-[[(1,1-dimethylethyl)dimethylsilyl]oxy]-3-fluoro-hexahydro-2H-cyclopenta[b]furan-2-ol By the procedure of Example 7 [3S-[3alpha,3a alpha,-4alpha (1E,3R*),5beta,6a alpha]]-4-[3-(1-fluorocyclopentyl)-3-[[(1,1-dimethylethyl)dimethylsilyl]oxy]-1-propenyl]-5-[[(1,1-dimethyl-ethyl)dimethylsilyl]oxy]-3-fluorohexahydro-2H-cyclopenta[b] furan-2-one was reduced to the oily [3S-[3alpha,3a alpha,4alpha(-1E,3R*),5beta, 6alpha]]-4-[3-(1-fluorocyclopentyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-ol Calc.: C, 60.86; H, 9.46; F, 7.13; Si, 10.54. Found: C, 60.92; H, 9.35; F, 6.85; Si, 10.71.

EXAMPLE 21

[1S-[1alpha(1R*,2Z),2beta(1E,3R*),3alpha,5alpha]]-7-[2-[3-(1-Fluorocyclopentyl)-3-[[(1,1-dimethylethyl)-dimethylsilyl]oxy]-1-propenyl]-3-[[(1,1-dimethylethyl)-dimethylsilyl]oxy]-5-hydroxycyclopentyl]-7-fluoro-5-heptenoic acid methyl ester By the procedure of Example 8 [3S-[3alpha,3a alpha,-4alpha (1E,3R*),5beta,6a alpha]]-4-[3-(1-fluorocyclopentyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-ol was condensed with the Wittig reagent derived from (4-carboxybutyl)triphenylphosphonium bromide to yield [1S-[1alpha(1R*,2Z),2beta(1E,3R*),3alpha, 5alpha]]-7-[2-[3-(1-fluorocyclopentyl)-3-[[(1,1-dimethylethyl)-dimethylsilyl]oxy]-1-propenyl]-3-[[(1,1-dimethylethyl)-dimethylsilyl]oxy]-5-hydroxycyclopentyl]-7-fluoro-5-heptenoic acid. This material was not purified but was reacted directly with ethereal diazomethane to give the oily [1S-1alpha(1R*,2Z),2beta(1E,3R*),3alpha,5alpha]-]-7-[2-[3-(1-fluorocyclopentyl)-3-[[(1,1-dimethylethyl)-=dimethylsilyl]oxy]-1-propenyl]-3-[[(1,1-dimethylethyl)=dimethylsilyl]oxy]-5-hydroxycyclopentyl]-7-fluoro-5-heptenoic acid methyl ester.

EXAMPLE 22

[3S-[3alpha,3a alpha,4alpha(1E,3R*),5beta,6a alpha]]-4-[3-(1-Fluorocyclopentyl)-3-[[(1,1-dimethylethyl)dimethylsilyl]oxy]-1-propenyl]-5-[[(1,1-dimethylethyl)dimethylsilyl]oxy]-3-fluorohexahydro-delta-iodo-2H-cyclopenta[b]furan-2-pentanoic acid methyl ester By the procedure of Example 9 [1S-[1alpha(1R*,2Z),-2beta (1E,3R*),3alpha,5alpha]]-7-[2-[3-(1-fluorocyclopentyl)-3-[[(1,1-dimethylethyl)dimethylsilyl]oxy]-1-propenyl]-3-]](1,1-dimethylethyl)dimethylsilyl]oxy]-5-hydroxycyclopentyl]-7-fluoro-5-heptenoic acid methyl ester was converted to [3S-[3alpha,3a alpha,4alpha(-1E,3R*),5beta,6a alpha]]-4-[3-(1-fluorocyclopentyl)-3-[[(1,1-dimethylethyl)=dimethylsilyl]oxy]-1-propenyl]-5-[[(1,1-dimethylethyl)= dimethylsilyl]oxy]-3-fluorohexahydro-delta-iodo-2H-cyclopenta[b]furan-2-pentanoic acid methyl ester.

EXAMPLE 23

[3S-[3alpha,3a alpha,4alpha(1E,3R*),5beta,6a alpha]]-4-[3-(1-Fluorocyclopentyl)-3-hydroxy-1-propenyl]-3-fluoro=hexahydro-5-hydroxy-delta-iodo-2H-cyclopenta[b[furan-2-pentanoic acid methyl ester By the procedure of Example 10 [3S-[3alpha,3a alpha, 4alpha(1E,3R*),5beta,6a alpha]]-4-[3-(1-fluorocyclopentyl)-3-[[(1,1-dimethylethyl)dimethylsilyl]oxy]-1-propenyl]-5-[[(1,1-dimethylethyl)dimethylsilyl]oxy]-3-fluorohexahydro-delta-iodo-2H-cyclopenta[b]furan-2-pentanoic acid methyl ester was converted to [3S-[3alpha,3a alpha,4alpha(1E,3R*), 5beta,6a alpha]]-4-[3-(1-fluorocyclpentyl)-3hydroxy-1-propenyl]-3-fluorohexahydro-5-hydroxy-delta-iodo-2H-cyclopenta[b]furan-2-pentanoic acid methyl ester, a viscous oil.

EXAMPLE 24

[3S-[(Z),3alpha,3a alpha,4alpha(1E,3R*),5beta,6a alpha]]-5-[4-[3-(1-Fluorocyclopentyl)-3-hydroxy-1-propenyl]-3-fluorohexahydro-5-hydroxy-2H-cyclopenta[b]furan-2-ylidene]-pentanoic acid methyl ester and [2S-[2alpha(4E),3alpha, 3a alpha,4alpha(1E,3R*),5beta,6a alpha]]-5-[4-[3-(1-fluorocyclopentyl-3-hydroxy-1-propenyl]-3-fluorohexahydro-5-hydroxycyclopenta[b-]furan-2-yl]-4-pentenoic acid methyl ester By the procedure of Example 11 [3S-[3alpha,3a alpha, 4alpha(1E,3R*),5beta,6a alpha]]-4-[3-(1-fluorocyclopentyl)-3-hydroxy-1-propenyl]-3-fluorohexahydro-5-hydroxy-delta-iodo-2 H-cyclopenta[b]furan-2-pentanoic acid methyl ester was converted to a mixture of products which upon separation by silica gel chromatography yielded [3S-[(Z),3alpha,3a alpha, 4alpha(-1E,3R*),5beta,6a alpha]]-5-[4-[3-(1-fluorocyclopentyl)-3-hydroxy-1-propenyl]-3-fluorohexahydro-5-hydroxy-2H-cyclopenta[b]furan-2-ylidene]pentanoic acid methyl ester and [2S-[2alpha(4E),3alpha,3a alpha,4alpha (1E,3R*),5beta,6a alpha]]-5-[4-[3-(1-fluorocyclopentyl)-3-hydroxy-1-propenyl]-3-fluorohexahydro-5-hydroxycyclopenta[b]furan-2-yl]-4-pentenoic acid methyl ester.

EXAMPLE 25

[3S-[(Z),3alpha,3a alpha,4alpha(1E,3R*),5beta,6a alpha]]-5-[4-[3-(1-Fluorocyclopentyl)-3-hydroxy-1-propenyl]-3-fluorohexahydro-5-hydroxy-2H-cyclopenta[b]furan-2-ylidene]-pentanoic acid sodium salt By the procedure of Example 12 [3S-[(Z),3alpha,3a alpha,4alpha(1E,3R*),5beta,6a alpha]]-5-[4-[3-(1-fluorocyclopentyl)-3-hydroxy-1-propenyl]-b 3-fluorohexahydro-5-hydroxy-2H-cyclopenta[b]furan-2-ylidene]pentanoic acid methyl ester was hydrolyzed to [3S-[(Z)-3alpha,3a alpha,4alpha(1E,3R*),5beta,6a alpha]]-5-[4-[3-(1-fluorocyclopentyl)-3-hydroxy-1-propenyl]-3-fluorohexahydro-5-hydroxy-2H-cyclopenta[b]furan-2-ylidene]-pentanoic acid sodium salt.

EXAMPLE 26

[2-(1-Methylcyclopentyl)-2-oxoethyl]phosphinic acid, dimethyl ester

By the procedure of Example 1, 1-methylcylcopentane carboxylic acid ethyl ester was converted to [2-(1-methylcyclopentyl)-2-oxoethyl]phosphinic acid dimethyl ester.

EXAMPLE 27

[3aR-[3a alpha,4alpha,(1E),5beta,6a alpha]]-5-(Benzoyloxy)-4-[3-(1-methylcyclopentyl)-3-oxo-1-propenyl]hexahydro-2H-cyclopenta[b]furan-2-one By the procedure of Example 2, [2-(1-methylcyclopentyl)-2-oxoethyl]phosphinic acid dimethyl ester was condensed with [3aR-[3a alpha,4alpha,5beta,6a alpha]]-5-(benzoyloxy)-hexahydro-4-formyl-2H-cyclopenta[b]furan-2-one to give [3aR-[3a alpha,4alpha,(1E),5beta,6a alpha]]-5-(benzoyloxy)-4-[3-(1-methylcyclopentyl)-3-oxo-1-propenyl]hexahydro-2H-cyclopenta[b]furan-2-one.

EXAMPLE 28

[3aR-[3a alpha,4alpha(1E,3R*),5beta,6a alpha]]-5-(Benzoyloxy)-4-[3-(1-methylcyclopentyl)-3-hydroxy-1-propenyl]hexahydro-2H-cyclopenta[b]furan-2-one By the procedure of Example 3 [3aR-[3a alpha,4alpha, (1E),5 beta,6a alpha]]-5-(benzoyloxy)-4-[3-(1-methylcyclopentyl)-3-oxo-1-propenyl]hexahydro-2H-cyclopenta[b]furan-2-one was converted by sodium borohydride reduction to a mixture of allylic alcohols. Silica gel chromatography of the reaction mixture yielded [3aR-[3a alpha,4alpha,(1E,3R*), 5beta,6a alpha]]-5-(benzoyloxy)-4-[3-(1-methylcyclopentyl)-3-hydroxy-1-propenyl]hexahydro-2H-cyclopenta[b]furan-2-one along with the 15β isomer [3aR-[3a alpha,4alpha,(1E,3S*), 5beta,6a alpha]]-5-(benzyloxy)-4-[3-(1-methylcyclopentyl)-3-hydroxy-1-propenyl]hexahydro-2H-cyclopenta[b]furan-2-one.

EXAMPLE 29

[3aR-[3a alpha,4alpha(1E,3R*),5beta,6a alpha]]-4-[3-(1-Methylcyclopentyl)-3-hydroxy-1-propenyl]hexahydro-5-hydroxy-2H-cyclopenta[b]furan-2-one By the procedure of Example 4 [3aR-[3a alpha,4alpha, (1E,3R*),5beta,6a alpha]]-5-(benzoyloxy)-4-[3-(1-methylcyclopentyl)-3-hydroxy-1-propenyl]hexahydro-2H-cyclopenta[b]furan-2-one was hydrolyzed to [3aR-[3a alpha,4alpha(1E,3R*),5beta, 6a alpha]]-4-[3-(1-methylcyclopentyl)-3-hydroxy-1-propenyl]-hexahydro-5-hydroxy-2H-cyclopenta[b]furan-2-one.

EXAMPLE 30

[3aR-[3a alpha,4alpha(1E,3R*),5beta,6a alpha]]-4-[3-(1-Methylcyclopentyl)-3-[[(1,1-dimethylethyl)dimethylsilyl]oxy]-1-propenyl]-5-[[(1,1-dimethylethyl)dimethylsilyl]oxy]hexahydro-2H-cyclopenta[b]furan-2-one By the procedure of Example 5 [3aR-[3a alpha,4alpha, (1E,3R*),5beta,6a alpha]]-4-[3-(1-methylcyclopentyl)-3-hydroxy-1-propenyl]hexahydro-5-hydroxy-2H-cyclopenta[b]furan-2-one was reacted with t-butyldimethylsilyl chloride to yield [3aR-[3a alpha,4alpha(1E,3R*),5 beta,6a alpha]]-4-[3-(1-methylcyclopentyl)-3-[[(1,1-dimethylethyl)dimethylsilyl]oxy]-1-propenyl]-5-[[(1,1-dimethylethyl)dimethylsilyl]oxy]-hexahydro-2H-cyclopenta[b]furan-2-one.

EXAMPLE 31

[3S-[3alpha,3a alpha,4alpha(1E,3R*),5beta,6a alpha]]-4-[3-(1-Methylcyclopentyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-one By the procedure of Example 6, [3aR-[3a alpha,4alpha, (1E,3R*),5beta,6a alpha]]-4-[3-(1-methylcyclopentyl)-3-[[(1,1-dimethylethyl)dimethylsilyl]oxy]-1-propenyl]-5-[[(1,1-dimethylethyl)dimethylsilyl]oxy]-hexahydro-2H-cyclopenta[b]furan-2-one was fluorinated with xenon difluoride to give [3S-[3alpha,3a alpha,4alpha(1E,3R*), 5beta,6a alpha]]-4-[3-(1-methylcyclopentyl)-3[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-one.

EXAMPLE 32

[3S-[3alpha,3a alpha,4alpha(1E,3R*),5beta,6a alpha]]-4-[3-(1-Methylcyclopentyl)-3-[[(1,1-dimethylethyl)dimethylsilyl]-oxy]-1-propenyl]-5-[[(1,1-dimethylethyl)dimethylsilyl]oxy]-3-fluorohexahydro-2H-cyclopenta[b]furan-2-ol By the procedure of Example 7, [3S-[3alpha,3a alpha,4alpha (1E,3R*),5beta,6a alpha]]-4-[3-(1-methylcyclopentyl)-3-[[(1,1-dimethylethyl)dimethylsilyl]oxy]-1-propenyl]-5-[[(1,1-dimethylethyl]dimethylsilyl]oxy]-3-fluorohexahydro-2H-cyclopenta[b]furan-2-one was reduced with Dibal-H to [3S-[3alpha,3a alpha,4alph-(1E,3R*),5betal,6a alpha]]-4-[3-(1-methylcyclopentyl-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-ol.

EXAMPLE 33

[1S-[1 alpha(1R*,2Z),2beta(1E,3R*),3alpha,5alpha]]-7-[2-(3-(1-Methylcyclopentyl)-3-[[(1,1-dimethylethyl)-dimethylsilyl]oxy]-1-propenyl]-3-[[(1,1-dimethylethyl) dimethylsilyl]oxy]-5-hydroxycyclopentyl]-7-fluoro-5-heptenoic acid methyl ester By the procedure of Example 8 [3S-[3alpha,3a alpha, 4alpha,(1E,3R*),5beta,6a alpha]]-4-[3-(1-methylcyclopentyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-ol was condensed with the Wittig reagent derived from (4-carboxybutyl)triphenylphosphonium bromide to yield [1S-[1 alpha(1R*,2Z),2beta(1E,3R*),3alpha, 5alpha]]-7-[2-[3-(1-methylcyclopentyl)-3-[[(1,1-dimethylethyl) dimethylsilyl]oxy]-1-propenyl]-3-[[(1,1-dimethylethyl) dimethylsilyl]oxy]-5-hydroxycyclopentyl]-7-fluoro-5-heptenoic acid methyl ester.

EXAMPLE 34

[3S-[3alpha,3a alpha,4alpha(1E,3R*),5beta,6a alpha]]-4-[3-(1-Methylcyclopentyl)-3-[[(1,1-dimethylethyl)dimethylsilyl]oxy]-1-propenyl]-5-[[(1,1-dimethylethyl)dimethylsilyl]oxy]-3-fluorohexahydro-delta-iodo-2H-cyclopenta[b]furan-2-pentanoic acid methyl ester By the procedure of Example 9, [1S-[1alpha,(1R*,2Z), 2beta (1E,3R*),3alpha,5alpha]]-7-[2-[3-(1-methylcyclopentyl)-3-[[(1,1-dimethylethyl)dimethylsilyl]oxy]-1-propenyl]-3-[[(1,1-dimethylethyl)dimethylsilyl]oxy]-5-hydroxycyclopentyl]-7-fluoro-5-heptenoic acid methyl ester was cyclized by reaction with N-iodosuccinimide to yield [3S-[3alpha,3a alpha,4alpha(1E,3R*),5beta,6a alpha]]-4-[3-(1-methylcyclopentyl)-3-[[(1,1-dimethylethyl)-dimethylsilyl]oxy]-1-propenyl]-5-[[(1,1-dimethylethyl)-dimethylsilyl]oxy]-3-fluorohexahydro-delta-iodo-2H-cyclopenta[b]furan-2-pentanoic acid methyl ester.

EXAMPLE 35

[3S-[3alpha,3a alpha,4alpha(1E,3R*),5beta,6a alpha]]-4-[3-(1-Methylcyclopentyl)-3-hydroxy-1-propenyl]-3-fluorohexahydro-5-hydroxy-delta-iodo-2H-cyclopenta[b]furan-2-pentanoic acid methyl ester By the procedure of Example 10, [3S-[3alpha,3a alpha, 4alpha,(1E,3R*),5beta,6a alpha]]-4-[3-(1-methyl cyclopentyl)-3-[[(1,1-dimethylethyl)dimethylsilyl]oxy]-1-propenyl]-5-[[(1,1-dimethylethyl)dimethylsilyl]oxy]-3-fluorohexahydrodelta-iodo-2H-cyclopenta[b]furan-2-pentanoic acid methyl ester was converted to [3S-[3alpha,3a alpha,4alpha(1E,3R*), 5beta,6a alpha]]-4-[3-(1-methylcyclopentyl)-3-hydroxy-1-propenyl]-3-fluorohexahydro-5-hydroxy-delta-iodo-2H-cyclopenta[b]furan-2-pentanoic acid methyl ester.

EXAMPLE 36

[3S-[(Z),3alpha,3a alpha,4alpha,(1E,3R*),5beta,6a alpha]]-5-[4-[3-(1-Methylcyclopentyl)-3-hydroxy-1-propenyl]-3-fluorohexahydro-5-hydroxy-2H-cyclopenta[b]furan-2-ylidene]pentanoic acid methyl ester and [2S-[2 alpha,(4E), 3alpha,3a alpha,4alpha,(1E,3R*),5beta,6a alpha]]-5-[4-[3-(1-Methylcyclopentyl)-3-hydroxy-1-propenyl]-3-fluorohexahydro-5-hydroxycyclopenta[b]furan-2-yl]-4-pentenoic acid methyl ester By the procedure of Example 11, [3S-[3 alpha,3a alpha, 4alpha,(1E,3R*),5beta,6a alpha]]-4-[3-(1-methylcyclopentyl)-3-hydroxy-1-propenyl]-3-fluorohexahydro-5-hydroxy-delta-iodo-2H-cyclopenta[b]furan-2-pentanoic acid methyl ester was converted with 1,8-diazobicyclo[5.4.0]undec-7-ene to a mixture of elimination products which upon separation by silica gel chromatography yielded [3S-(Z),3alpha,3a alpha,4alpha, (1E,3R*),5beta,6a alpha]]-5-[4-[3-(1-methylcyclopentyl)-3-hydroxy-1-propenyl]-3-fluorohexahydro-5-hydroxy-2H-cyclopenta[b]furan-2-ylidene]pentanoic acid methyl ester and [2S-[2alpha,(4E),3alpha,3a alpha,-4alpha,(1E,3R*),5beta,6a alpha]]-5-[4-[3-(1-methylcyclopentyl)-3-hydroxy-1-propenyl]-3-fluorohexahydro-5-hydroxycyclopenta[b]furan-2-yl]-4-pentenoic acid methyl ester.

EXAMPLE 37

3S-[(Z),3alpha,3a alpha,4alpha,(1E,3R*),5beta,6a alpha]]-5-[4-[3-(1-Methylcyclopentyl)-3-hydroxy-1-propenyl]-3-fluorohexahydro-5-hydroxy-2H-cyclopenta[b]furan-2-ylidene]pentanoic acid sodium salt By the procedure of Example 12, [3S-[(Z),3alpha,3a alpha,4alpha,(1E,3R*),5beta,6a alpha]]-5-[4-[3-(1-methylcyclopentyl)-3-hydroxy-1-propenyl]-3-fluorohexahydro-5-hydroxy-2H-cyclopenta[b]furan-2-ylidene]pentanoic acid methyl ester was hydrolyzed with sodium hydroxide to [3S-[(Z),3alpha,3a alpha,4alpha,(1E,3R*),5beta,6a alpha]]-5-[4-[3-(1-methylcyclopentyl)-3-hydroxy-1-propenyl]-3-fluorohexahydro-5-hydroxy-2H-cyclopenta[b]furan-2-ylidene]pentanoic acid sodium salt.

EXAMPLE 38

1-Fluorocyclohexanecarboxylic acid ethyl ester

By the procedure of Example 13, cyclohexane carboxylic acid ethyl ester was fluorinated with perchlorylfluoride to yield 1-fluorocyclohexanecarboxylic acid ethyl ester.

EXAMPLE 39

[2-(1-Fluorocyclohexyl)-2-oxoethyl]phosphonic acid dimethyl ester

By the procedure of Example 1, 1-fluorocyclohexane carboxylic acid ethyl ester was converted to [2-(1-fluorocyclohexyl)-2-oxoethyl]phosphonic acid dimethyl ester.

EXAMPLE 40

[3aR-[3a alpha,4alpha,(1E),5beta,6a alpha]]-5-(Benzoyloxy)-4-[3-(1-fluorocyclohexyl)-3-oxo-1-propenyl]hexahydro-2H-cyclopenta[b]furan-2-one By the procedure of Example 2, [2-(1-fluorocyclohexyl)-2-oxoethyl]phosphonic acid dimethyl ester was condensed with [3aR-[3a alpha,4alpha,5beta,6a alpha]]-5-(benzoyloxy)hexahydro-4-formyl-2H-cyclopenta[b]furan-2-one to give [3aR-[3a alpha,4alpha,(1E),5beta,6a alpha]]-5-(benzoyloxy)-4-[3-(1-fluorocyclohexyl)-3-oxo-1-propenyl]hexahydro-2H-cyclopenta[b]furan-2-one.

EXAMPLE 41

[3aR-[3a alpha,4alpha,(1E,3R*),5beta,6a alpha]]-5-(Benzoyloxy)-4-[3-(1-fluorocyclohexyl)-3-hydroxy-1-propenyl]hexahydro-2H-cyclopenta[b]furan-2-one, and [3aR-[3a alpha,4alpha,(1E,3S*),5beta,6a alpha]]-5-(benzoyloxy)-4-[3-(1-fluorocyclohexyl)-3-hydroxy-1-propenyl]hexahydro-2H-cyclopenta[b]furan-2-one By the procedure of Example 3, [3aR-[3a alpha,4alpha, (1E), 5beta,6a alpha]]-5-(benzoyloxy)-4-[3-(1-fluorocyclohexyl)-3-oxo-1-propenyl]hexahydro-2H-cyclopenta[b]furan-2-one was reduced with sodium borohydride to give a mixture which was separated by silica gel chromatography to yield [3aR-[3a alpha,4alpha,(1E,3R*), 5beta,6a alpha]]-5-(benzoyloxy)-4-[3-(1-fluorocyclohexyl)-3-hydroxy-1-propenyl]hexahydro-2H-cyclopenta[b]furan-2-one, and the more polar 15β isomer [3aR-[3a alpha,4alpha,(1E,3S*),5beta,6a alpha]]-5-(benzoyloxy)-4-[3-(1-fluorocyclohexyl)-3-hydroxy-1-propenyl]=hexahydro-2H-cyclopenta[b]furan-2-one.

EXAMPLE 42

[3aR-[3a alpha,4alpha(1E,3R*),5beta,6a alpha]]-4-[3-(1-fluorocyclohexyl)-3-hydroxy-1-propenyl]hexahydro-5-hydroxy-2H-cyclopenta[b]furan-2-one By the procedure of Example 4, [3aR-[3a alpha,4alpha, (1E,3R*),5beta,6a alpha]]-5-(benzoyloxy)-4-[3-(1-fluorocyclohexyl)-3-hydroxy-1-propenyl]hexahydro-2H-cyclopenta[b]furan-2-one was converted to [3aR-[3a alpha, 4alpha(1E,3R*),5beta,6a alpha]]-4-[3-(1-fluorocyclohexyl)-3-hydroxy-1-propenyl]hexahydro-5-hydroxy-2H-cyclopenta[b]furan-2-one.

EXAMPLE 43

[3aR-[3a alpha,4alpha(1E,3R*),5beta,6a alpha]]-4-[3-(1-fluorocyclohexyl)-3-[[1,1-dimethylethyl)dimethylsilyl]oxy]-1-propenyl]-5-[[(1,1-dimethylethyl)dimethylsilyl]oxy]hexahydro-2H-cyclopenta[b]furan-2-one By the procedure of Example 5, [3aR-[3a alpha,4alpha (1E,3R*),5beta,6a alpha]]-4-[3-(1-fluorocyclohexyl)-3-hydroxy-1-propenyl]hexahydro-5-hydroxy-2H-cyclopenta[b]furan-2-one was converted to [3aR-[3a alpha,4alpha(1E,3R*),5 beta, 6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]hexahydro-2H-cyclopenta[b]furan-2-one.

EXAMPLE 44

3S-[3alpha,3a alpha,4alpha(1E,3R*),5beta,6a alpha]]-4-[3-(1-Fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-one By the procedure of Example 6, [3aR-[3a alpha,4alpha (1E,3R*),5beta,6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]-hexahydro-2H-cyclopenta[b]furan-2-one was fluorinated to produce [3S-[3alpha,3a alpha, 4alpha(1E,3R*),-5beta,6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-one.

EXAMPLE 45

[3S-[3alpha,3a alpha,4alpha(1E,3R*),5beta,6a alpha]]-4-[3-(1-Fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-ol By the procedure of Example 7, [3S-[3alpha,3a alpha,4alpha (1E,3R*),5beta,6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-one was reduced with Dibal-H (diisobutyl aluminum hydride) to [3S-[3 alpha,3a alpha,4alpha (1E,3R*),5beta,6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-ol.

EXAMPLE 46

[1S-[1alpha(1R*,2Z)2beta(1E,3R*)3alpha,5alpha]]-7-[2--[3-(1-Fluorocyclohexyl)-3-[[(1,1-dimethylethyl)dimethylsilyl]oxy]-1-propenyl]-3-[[(1,1-dimethylethyl)dimethylsilyl]oxy]-5-hydroxycyclopentyl]-7-fluoro-5-heptenoic acid methyl ester By the procedure of Example 8 [3S-[3alpha,3a alpha, 4alpha(1E,3R*)5beta,6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-2H-cyclopenta[b]furan-2-ol was condensed with the Wittig reagent derived from (4-carboxybutyl)triphenylphosphonium bromide to yield [1S-[1 alpha,(1R*,2Z) 2beta (1E,3R*) 3alpha,5alpha]]-7-[2-[3-(1-fluorocyclohexyl)-3-[[(1,1-dimethylethyl)dimethylsilyl]oxy]-1-propenyl]-3-[[(1,1-dimethylethyl)dimethylsilyl]oxy]-5-hydroxycyclopentyl]-7-fluoro-5-heptenoic acid. This material was not purified but was reacted directly with diazomethane to give [1S-[1alpha (1R*,2Z)2beta(1E,3R*)3alpha,5alpha]]-7-[2-[3-(1-fluorocyclohexyl)-3-[[(1,1-dimethylethyl)dimethylsilyl]oxy]-1-propenyl]-3-[[(1,1-dimethylethyl)dimethylsilyl]oxy]-5-hydroxycyclopentyl]-7-fluoro-5-heptenoic acid methyl ester.

EXAMPLE 47

[3S-[3alpha,3a alpha,4alpha(1E,3R*)5beta,6a alpha]]-4-[3-(1-Fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-delta-iodo-2H-cyclopenta[b]furan-2-pentanoic acid methyl ester By the procedure of Example 9 [1S-[1 alpha,(1R*,2Z)2beta (1E,3R*)3alpha,5alpha]]-7-[2-[3-(1-fluorocyclohexyl)-3-[[(1,1-dimethylethyl)dimethylsilyl]oxy]-1-propenyl]-3-[[(1,1-dimethylethyl)dimethylsilyl]oxy]-5-hydroxycyclopentyl]-7-fluoro-5-heptenoic acid methyl ester was converted to [3S-[3alpha,3a alpha,4alpha(1E,3R*)5beta,6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-delta-iodo-2H-cyclopenta[b]furan-2-pentanoic acid methyl ester.

EXAMPLE 48

[3S-[3alpha,3a alpha,4alpha(1E,3R*)5beta,6a alpha]]-3-[3](1-Fluorocyclohexyl)-3-hydroxy-1-propenyl]-3-fluorohexahydro-5-hydroxy-delta-iodo-2H-cyclopenta[b]furan-2-pentanoic acid methyl ester By the procedure of Example 10, [3S-[3alpha,3a alpha, 4alpha(1E,3R*)5beta,6a alpha]]-4-[3-(1-fluorocyclohexyl)-3-[[(1,1-dimethylethyl)dimethylsilyl]oxy]-1-propenyl]-5-[[(1,1-dimethylethyl)dimethylsilyl]oxy]-3-fluorohexahydro-delta-iodo-2H-cyclopenta[b]furan-2-pentanoic acid methyl ester was converted to [3S-3alpha,3a alpha,4alpha(1E,3R*)5beta,6a alpha]]-4-[3-(1-fluorocyclohexyl)-3-hydroxy-1-propenyl]-3-fluorohexahydro-5-hydroxy-delta-iodo-2H-cyclopenta[b]furan-2-pentanoic acid methyl ester.

EXAMPLE 49

[3S-[(Z),3alpha,3a alpha,4alpha(1E,3R*)5beta,6a alpha]]-5-[4-[3-(1-Fluorocyclohexyl)-3-hydroxy-1-propenyl]-3-fluorohexahydro-5-hydroxy-2H-cyclopenta[b]furan-2-ylidene]-pentanoic acid methyl ester and [2S-[2alpha,(4E),3alpha,3a alpha,4alpha(1E,3R*),5beta,6a alpha]]-5-[4-[3-(1-fluorocyclohexyl)-3-hydroxy-1-propenyl]-3-fluorohexahydro-5-hydroxycyclopenta[b-]furan-2-yl]-4-pentenoic acid methyl ester By the procedure of Example 11, [3S-[3alpha,3a alpha,4alpha(1E,3R*),5beta,6a alpha]]-4-[3-(1-fluorocyclohexyl)-3-hydroxy-1-propenyl]-3-fluorohexahydro-5-hydroxy-delta-iodo-2H-cyclopenta[b]furan-2-pentanoic acid methyl ester was converted to a mixture of elimination products which upon separation by silica gel chromatography yielded [3-[(Z),3alpha,3a alpha,4alpha(-1E,3R*),5beta,6a alpha]]-5-[4-[3-(1-fluorocyclohexyl)-3-hydroxy-1-propenyl]-3-fluorohexahydro-5-hydroxy-2H-cyclopenta[b]furan-2-ylidene]pentanoic acid methyl ester and [2S-[2alpha(4E),3alpha,3a alpha,4alpha(-1E,3R*),5beta,6a alpha]]-5-[4-[3-(1-fluorocyclohexyl)-3-hydroxy-1-propenyl]-3-fluorohexahydro-5-hydroxycyclopenta[b]furan-2-yl]4-pentenoic acid methyl ester.

EXAMPLE 50

[3S-[(Z),3alpha,3a alpha,4alpha(1E,3R*),5beta,6aa alpha]]-5-[4-[3-(1-Fluorocyclohexyl)-3-hydroxy-1-propenyl]-3-fluorohexahydro-5-hydroxy-2H-cyclopenta[b]furan-2-ylidene]pentanoic acid sodium salt By the procedure of Example 12 [3S-[(Z),3alpha,3a alpha,4alpha(1E,3R*),5beta,6a alpha]]-5-[4-[3-(1-fluorocyclohexyl)-3-hydroxy-1-propenyl]-3-fluorohexahydro-5-hydroxy-2H-cyclopenta[b]furan-2-ylidene]-pentanoic acid methyl ester was hydrolyzed to [3S-[(Z),3alpha,3a alpha,4alpha(1E,3R*),5beta,6a alpha]]-5-[4-[3-(1-fluorocyclohexyl)-3-hydroxy-1-propenyl]-3-fluorohexahydro-5-hydroxy-2H-cyclopenta[b]furan-2-ylidene]pentanoic acid sodium salt.

EXAMPLE 51

[3S-[(Z),3 alpha, 3a alpha, 4 alpha (1E,3R*) 5beta, 6a alpha]]-5-[3-Fluorohexahydro-5-acetoxy-4-[3-acetoxy-3-1-methylcyclohexyl]-1-propenyl]-2H-cyclopenta[b-]furan-2-ylidene]pentanoic acid methyl ester To a solution of 50 mg (124 μmol) of (3S-[(Z) 3 alpha, 3a alpha, 4 alpha (1E,2R*), 5 beta, 6a alpha]]-5-[3-fluorohexahydroxy-b 3-(1-methylcyclohexyl-1-propenyl)]-2H-cyclopenta[b]furan-2-ylidene]pentanoic acid methyl ester in 2 ml of pyridine cooled to 0° C. was added 300 μl of acetic anhydride. The reaction mixture was stirred for one hour at 0° C. and then for two hours at room temperature. A small amount of methanol was then added to the chilled solution and the mixture then poured into 2 ml of 0.1N HCl. The resulting mixture was then extracted with ethyl acetate, the organic layer separated, and then washed with a saturated sodium bicarbonate solution followed by a saturated sodium chloride solution. The ethyl acetate solution was then dried (MgSO4) and the solvent removed under vacuum. The residue was then chromatographed on 12 g of silica gel and eluted with a ethyl acetate/hexane solution to give 46.7 mg (95.9 μmol) 77.3% of [3S,[(Z) 3 alpha, 3a alpha, 4 alpha (1E,3R*), 5 beta, 6a alpha]]-5-[3-fluorohexahydro-5-acetoxy-4-[3-acetoxy-3-(1-methyl-cyclohexyl-1-propenyl)]-2H-cyclopenta[b]furan-2-ylidene]pentanoic acid methyl ester.

EXAMPLE 52

[3S-[(Z),3 alpha, 3a alpha, 4 alpha (1E,3R*), 5 beta, 6a alpha]]-5-[4-[3-(1-Methylcyclopentyl)-3-acetoxy-1-propenyl]-3-fluorohexahydro-5-acetoxy-2H-cyclopenta[b]fran-2-ylidene]pentanoic acid methyl ester By the procedure of Example 51, [3S-[(Z), 3 alpha, 3a alpha, 4 alpha, (1E,3R*), 5 beta, 6a alpha], [4-[3-(1-methylcyclopentyl)-3-hydroxy-1-propenyl]-3-fluorohexahydro-5-hydroxy-2H-cyclopenta[b]furan-2-ylidene]pentanoic acid methyl ester was converted to [3S-[(Z),3 alpha,3a alpha,4 alpha,(1E,3R*),5 beta,6a alpha]]-5-[4-[3-(1-methylcyclopentyl)-3-acetoxy-1-propenyl]-3-fluorohexahydro-5-acetoxy-2H-cyclopenta[b]furan-2-ylidene]-pentanoic acid methyl ester.

EXAMPLE 53

[3S-[(Z),3alpha,3a alpha,4 alpha(1E,3R*)5 beta,6a alpha]]-5-[4-[3-(1-Fluorocyclohexyl)-3-acetoxy-1-propenyl]-3-fluorohexahydro-5-acetoxy-2H-cyclopenta[b]furan-2-ylidene]pentanoic acid methyl ester By the procedure of Example 51, [3S-[(Z),3 alpha,3a alpha,4 alpha(1E,3R*)5 beta,6a alpha]]-4-[4-[3-(1-fluorocyclohexyl)-3-hydroxy-1-propenyl]-3-fluorohexahydro-5-hydroxy-2H-cyclopenta[b]furan-2-ylidene]-pentanoic acid methyl ester was converted to [3S-[(Z),3 alpha,3a alpha,4 alpha(1E,3R*)5 beta,6a alpha]]-5-[4-[3-(1-fluorocyclohexyl)-3-acetoxy-1-propenyl]-3-fluorohexahydro-5-acetoxy-2H-cyclopenta[b]furan-2-ylidene]-pentanoic acid methyl ester.

EXAMPLE 54

[3S-[(Z),3 alpha,3a alpha,4 alpha(1E,3R*)5 beta,6a alpha]]-5-[4-[3-(1-Fluorocyclopentyl)-3-acetoxy-1-propenyl]-3-fluorohexahydro-5-acetoxy-2H-cyclopenta[b]furan-2-ylidene]pentanoic acid methyl ester By the procedure of Example 51, [3S-[(Z),3 alpha,3a alpha,4 alpha(1E,3R*)5 beta,6a alpha]]-4-[4-[3-(1-fluorocyclopentyl)-3-hydroxy-1propenyl]-3-fluorohexahydro-5-hydroxy-2H-cyclopenta[b]furan-2-ylidene]-pentanoic acid methyl ester was converted to [3S-[(Z),3 alpha,3a alpha,4 alpha (1E,3R*)5 beta,6a alpha]]-5-[4-[3-(1-fluorocyclopentyl)-3-acetoxy-1-propenyl]-3-fluorohexahydro-5-acetoxy-2H-cyclopenta[b]furan-2-ylidene]pentanoic acid methyl ester.

EXAMPLE 55

Cream 0.05%

The following is the quantitative composition of drug:

| Ingredients | g/kg | Reasonable Variations |
|---|---|---|
| [3S—[(Z),3alpha,3a alpha, 4alpha(1E,3R*),5beta,6a alpha]]]-5-[3-fluorohexahydro-5-hydroxy-4-[3-hydroxy-3-(1-methylcyclohexyl)-1-propenyl]-2H—cyclopenta[b]furan-2-ylidene]pentanoic acid methyl ester | 0.525* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methyl Paraben | 1.50 | 1.25–1.75 |
| Propyl Paraben | 0.50 | 0.4–0.6 |

-continued

| Ingredients | g/kg | Reasonable Variations |
|---|---|---|
| Propylene Glycol | 200.00 | 150-250 |
| Purified Water | 574.055 | 525-625 |
| Total | 1016.58 gm | |

[1] Arlacel 165
[2] Tween 60
*3% excess of drug

EXAMPLE 56

Cream 0.05%

The following is the quantitative composition of drug:

| Ingredients | g/kg | Reasonable Variations |
|---|---|---|
| 3S—[(Z),3alpha,3a alpha, 4alpha(1E,3R*),5beta,6a alpha]]-5-[3-fluorohexahydro-5-hydroxy-4-[3-hydroxy-3-(1-methylcyclohexyl)-1-propenyl]-2H—cyclopenta[b]furan-2-ylidene]pentanoic acid, sodium salt | 0.525* | — |
| Glyceryl Monostearate S.E.[1] | 100.00 | 80-120 |
| Polysorbate 60[2] | 20.00 | 15-25 |
| Cetyl Alcohol | 50.00 | 40-60 |
| Petrolatum | 70.00 | 50-90 |
| Methyl Paraben | 1.50 | 1.25-1.75 |
| Propyl Paraben | 0.50 | 0.4-0.6 |
| Propylene Glycol | 200.00 | 150-250 |
| Purified Water | 574.055 | 525-625 |
| Total | 1016.58 gm | |

[1] Arlacel 165
[2] Tween 60
*3% excess of drug

EXAMPLE 57

Cream 0.25%

The following is the quantitative composition of drug:

| Ingredients | g/kg | Reasonable Variations |
|---|---|---|
| [3S—[(Z),3alpha,3a alpha, 4alpha(1E,3R*),5beta,6a alpha]]-5-[4-[3-(1-Fluorocyclopentyl)-3-hydroxy-1-Propenyl]-3-fluorohexahydro-5-hydroxy-2H—cyclopenta[b]furan-2-ylidene]pentanoic acid salt | 2.575* | — |
| Glyceryl Monostearate S.E.[1] | 100.00 | 80-120 |
| Polysorbate 60[2] | 20.00 | 15-25 |
| Cetyl Alcohol | 50.00 | 40-60 |
| Petrolatum | 70.00 | 50-90 |
| Methyl Paraben | 1.50 | 1.25-1.75 |
| Propyl Paraben | 0.50 | 0.4-0.6 |
| Propylene Glycol | 200.00 | 150-250 |
| Purifled Water | 571.395 | 500-600 |
| Total | 1015.97 gm | |

[1] Arlacel 165
[2] Tween 60
*3% excess of drug

EXAMPLE 58

Cream 0.25%

The following is the quantitative composition of drug:

| Ingredients | g/kg | Reasonable Variations |
|---|---|---|
| [3S—[(Z),3alpha,3a alpha, 4alpha(1E,3R*),5beta,6a alpha]]-5-[4-[3-(1-fluorocyclohexyl)-3-hydroxy-1-propenyl]-3-fluorohexahydro-5-hydroxy-2H—cyclopenta[b]furan-2-ylidene]pentanoic acid sodium salt | 2.575* | — |
| Glyceryl Monostearate S.E.[1] | 100.00 | 80-120 |
| Polysorbate 60[2] | 20.00 | 15-25 |
| Cetyl Alcohol | 50.00 | 40-60 |
| Petrolatum | 70.00 | 50-90 |
| Methyl Paraben | 1.50 | 1.25-1.75 |
| Propyl Paraben | 0.50 | 0.4-0.6 |
| Propylene Glycol | 200.00 | 150-250 |
| Purified Water | 571.395 | 500-600 |
| Total | 1015.97 gm | |

[1] Arlacel 165
[2] Tween 60
*3% excess of drug

EXAMPLE 59

Capsule Formulation

| Ingredients | mg/cap | | | |
|---|---|---|---|---|
| 1. [3S—[(Z),3alpha, 3a alpha,4alpha (1E,3R*),5beta,6a alpha]]-5-[3-Fluorohexahydro-5-hydroxy-4-[3-hydroxy-3-(1-methylcyclohexyl)-1-propenyl]-2H—cyclopenta[b]furan-2-ylidene] pentanoic acid, sodium salt | 0.01 | 0.5 | 5.0 | 25.0 |
| 2. Lactose Hydrose | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Mg stearate | 1.0 | 1.0 | 1.0 | 2.0 |
| | 200.0 | 200.0 | 200.0 | 200.0 |

Manufacturing Procedure
1. Mix items 1, 2, and 3 in a suitable mixer for 30 minutes.
2. Add items 4 and 5 and mix for 3 minutes.
3. Fill in suitable capsule.

EXAMPLE 60

Capsule Formulation

| Ingredient | mg/cap | | | |
|---|---|---|---|---|
| 1. [3S—[(Z),3alpha, 3a alpha,4alpha (1E,3R*),5beta,6a alpha]]-5-[4-[3-(1-Fluorocyclopentyl)-3-hydroxy-1-propenyl]-3-fluorohexahydro-5-hydroxy-2H—cyclopenta[b]furan-2-ylidene]pentanoic acid methyl ester | 0.01 | 0.5 | 5.0 | 25.0 |
| 2. Lactose Hydrose | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Mg stearate | 1.0 | 1.0 | 1.0 | 2.0 |
| | 200.0 | 200.0 | 200.0 | 200.0 |

Manufacturing Procedure
1. Mix items 1, 2, and 3 in a suitable mixer for 30 minutes.
2. Add items 4 and 5 and mix for 3 minutes.
3. Fill in suitable capsule.

EXAMPLE 61

Capsule Formulation

| Ingredients | mg/cap | | | |
|---|---|---|---|---|
| 1. [3S—[(Z),3alpha, 3a alpha,4alpha (1E,3R*),5beta,6a alpha]]-5-[4-[3-(1-Fluorocyclo-hexyl)-3-hydroxy-1-propenyl]-3-fluorohexahydro-5-hydroxy-2H—cyclopenta[b]furan-2-ylidene]pentanoic acid sodium salt | 0.01 | 0.5 | 5.0 | 25.0 |
| 2. Lactose Hydrose | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Mg stearate | 1.0 | 1.0 | 1.0 | 2.0 |
| | 200.0 | 200.0 | 200.0 | 200.0 |

Manufacturing Procedure
1. Mix items 1, 2, and 3 in a suitable mixer for 30 minutes.
2. Add items 4 and 5 and mix for 3 minutes.
3. Fill in suitable capsule.

We claim:

1. A prostacyclin selected from the group consisting of a compound of the formula

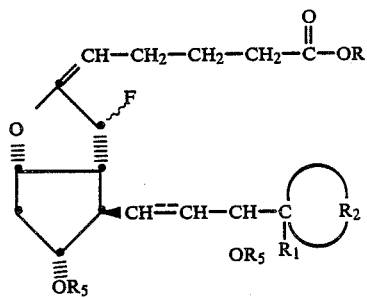

I-A wherein R is hydrogen or lower alkyl; $R_5$ is hydrogen or lower alkanoyl; $R_1$ is fluoro and $R_2$ taken together with its attached carbon atom forms a cycloalkyl ring of from 3 to 7 carbon atoms and the dotted bond is optionally hydrogenated; pharmaceutically acceptable salts, optical antipodes, diastereoisomers and racemates thereof.

2. The prostacyclin of claim 1 wherein $R_2$ forms a six membered cycloalkyl ring.

3. The prostacyclin of claim 2 wherein $R_1$ is fluoro.

4. The prostacyclin of claim 3 where the dotted bond is not hydrogenated.

5. The prostacyclin of claim 4 wherein said compound is 5-[4-[3-(1-fluorocyclohexyl)-3-hydroxy-1-propenyl]-3-fluorohexahydro-5-hydroxy-2H-cyclopenta[b]furan-2-ylidene]pentanoic acid methyl ester.

6. The prostacyclin of claim 4 wherein said compound is [5-[3-(1-fluorocyclohexyl)-3-hydroxy-1-propenyl]-3-fluorohexahydro-5-hydroxy-2H-cyclopenta[b]furan-2-ylidene]pentanoic acid.

7. The prostacyclin of claim 4 wherein said compound is 5-[4-[3-(1-fluorocyclohexyl)-3-acetoxy-1-propenyl]-3-fluorohexahydro-5-acetoxy-2H-cyclopenta[b]furan-2-ylidene]pentanoic acid methyl ester.

8. The prostacyclin of claim 1 wherein $R_2$ forms a five membered cycloalkyl ring.

9. The prostacyclin of claim 8 wherein the dotted bond is not hydrogenated.

10. The prostacyclin of claim 9 wherein $R_1$ is fluoro.

11. The prostacyclin of claim 10 wherein said compound is 5-[4-[3-(1-fluorocyclopentyl)-3-hydroxy-1-propenyl]-3-fluorohexahydro-5-hydroxy-2H-cyclopenta[b]furan-2-ylidene]-pentanoic acid.

12. The prostacyclin of claim 10 wherein said compound is 5-[4-[3-(1-fluorocyclopentyl)-3-hydroxy-1-propenyl]-3-fluorohexahydro-5-hydroxy-2H-cyclopenta[b]furan-2-ylidene]pentanoic acid methyl ester.

13. The prostacyclin of claim 10 wherein said compound is 5-[4-[3-(1-fluorocyclopentyl)-3-acetoxy-1-propenyl]-3-fluorohexahydro-5-acetoxy-2H-cyclopenta[b]furan-2-ylidene]pentanoic acid methyl ester.

* * * * *